US012806298B2

(12) United States Patent
Fisher et al.

(10) Patent No.: US 12,806,298 B2
(45) Date of Patent: Nov. 24, 2026

(54) ELECTRON BEAM INTEGRATION FOR STERILIZING RADIOPHARMACEUTICALS INSIDE A HOT CELL

(71) Applicant: BWXT Advanced Technologies LLC, Lynchburg, VA (US)

(72) Inventors: Benjamin D. Fisher, Lynchburg, VA (US); Curtis G. Hamilton, Greensboro, NC (US); Kenneth Palazzi, Forest, VA (US)

(73) Assignee: BWXT Advanced Technologies LLC, Lynchburg, VA (US)

( * ) Notice: Subject to any disclaimer, the term of this patent is extended or adjusted under 35 U.S.C. 154(b) by 472 days.

(21) Appl. No.: 18/199,237

(22) Filed: May 18, 2023

(65) Prior Publication Data

US 2023/0372556 A1 Nov. 23, 2023

Related U.S. Application Data

(60) Provisional application No. 63/343,780, filed on May 19, 2022.

(51) Int. Cl.
*A61L 2/087* (2026.01)
*A61L 103/05* (2026.01)

(52) U.S. Cl.
CPC ........... *A61L 2/087* (2013.01); *A61L 2103/05* (2026.01); *A61L 2202/122* (2013.01); *A61L 2202/14* (2013.01)

(58) Field of Classification Search
CPC ................. A61L 2/087; A61L 2103/05; A61L 2202/122; A61L 2202/14; A61L 2202/121
See application file for complete search history.

(56) References Cited

U.S. PATENT DOCUMENTS 3,286,095 A 11/1966 Lane
4,448,750 A 5/1984 Fuesting
4,652,763 A 3/1987 Nablo
5,695,443 A 12/1997 Brent et al.
5,712,894 A 1/1998 Lanotte
5,958,336 A 9/1999 Duarte
(Continued)

FOREIGN PATENT DOCUMENTS

WO 2020249234 A1 12/2020
WO 2021004678 A1 1/2021
(Continued)

OTHER PUBLICATIONS

International Search Report and Written Opinion for corresponding PCT application, PCT/US2023/22821, dated Oct. 6, 2023, 17 pages.

*Primary Examiner* — Brendan A Hensel
(74) *Attorney, Agent, or Firm* — Nelson Mullins Riley & Scarborough LLP

(57) ABSTRACT

A sterilization system for a radiopharmaceutical product comprising a hot cell disposed within a clean room environment. A sterilization shaft extends between a first end and a second end and defines an interior. The first end of the shaft is disposed within the hot cell and the second end of the shaft is disposed externally to the clean room. An electron beam accelerator assembly is disposed within the interior of the sterilization shaft so that an emission end of the electron beam accelerator is adjacent the first end of the sterilization shaft.

15 Claims, 24 Drawing Sheets

(56) References Cited

U.S. PATENT DOCUMENTS

| | | | |
|---|---|---|---|
| 6,396,065 B1 | 5/2002 | Kimura et al. | |
| 6,407,492 B1 | 6/2002 | Avnery et al. | |
| 6,436,343 B1 | 8/2002 | Bechini | |
| 6,680,482 B1 | 1/2004 | Perrins et al. | |
| 6,844,689 B1 | 1/2005 | Brown et al. | |
| 6,897,245 B2 | 5/2005 | Gen | |
| 7,150,853 B2 | 12/2006 | Lee et al. | |
| RE39,657 E | 5/2007 | Wakalopulos et al. | |
| 7,282,726 B2 | 10/2007 | Usami et al. | |
| 7,348,555 B2 | 3/2008 | Usami et al. | |
| 7,394,081 B2 | 7/2008 | Okazaki et al. | |
| 7,520,108 B2 | 4/2009 | Kristiansson et al. | |
| 7,577,228 B2 | 8/2009 | Jackson | |
| 7,727,464 B2 | 6/2010 | Frost | |
| 7,825,392 B2 | 11/2010 | Prosser | |
| 8,203,124 B2 | 6/2012 | Havens et al. | |
| 8,293,173 B2 | 10/2012 | Bufano et al. | |
| 9,072,803 B2 | 7/2015 | Sakaki | |
| 9,107,968 B2 | 8/2015 | Knott et al. | |
| 9,302,896 B2 | 4/2016 | Drenguis et al. | |
| 9,651,680 B2 | 5/2017 | Stagg et al. | |
| 9,682,162 B2 | 6/2017 | Freeman et al. | |
| 9,682,163 B2 | 6/2017 | Loy et al. | |
| 9,775,923 B2 | 10/2017 | Knott et al. | |
| 9,812,282 B2 | 11/2017 | Brown et al. | |
| 9,907,867 B2 | 3/2018 | Eriksson et al. | |
| 10,078,772 B2 | 9/2018 | Petrofsky et al. | |
| 10,081,448 B2 | 9/2018 | Yokobayashi | |
| 10,361,009 B2 | 7/2019 | Brown et al. | |
| 10,406,252 B2 | 9/2019 | Graves et al. | |
| 10,535,441 B1 | 1/2020 | Brown et al. | |
| 10,874,754 B2 | 12/2020 | Boysset et al. | |
| 11,072,106 B2 | 7/2021 | Martini et al. | |
| 11,129,941 B2 | 9/2021 | Tan-Malecki et al. | |
| 11,286,172 B2 | 3/2022 | Russell, II et al. | |
| 11,298,463 B2 | 4/2022 | Tan-Malecki et al. | |
| 11,391,853 B2 | 7/2022 | Fewox et al. | |
| 11,485,030 B2 | 11/2022 | Bechini et al. | |
| 2003/0091646 A1 | 5/2003 | Gen | |
| 2005/0247893 A1 | 11/2005 | Fu et al. | |
| 2006/0153732 A1 | 7/2006 | Lee et al. | |
| 2012/0025105 A1 | 2/2012 | Brown et al. | |
| 2012/0251386 A1 | 10/2012 | Wootton et al. | |
| 2014/0112826 A1* | 4/2014 | Knott | A61L 2/087 250/453.11 |
| 2015/0343480 A1 | 12/2015 | Byrne et al. | |
| 2016/0251099 A1* | 9/2016 | Poppi | A61L 2/087 250/454.11 |
| 2016/0376040 A1 | 12/2016 | Bingham et al. | |
| 2017/0251547 A1 | 8/2017 | Ito | |
| 2017/0321244 A1 | 11/2017 | Verma et al. | |
| 2017/0323696 A1 | 11/2017 | Kani et al. | |
| 2018/0200395 A1 | 7/2018 | Graves et al. | |
| 2018/0244535 A1 | 8/2018 | Russell, II et al. | |
| 2018/0244536 A1 | 8/2018 | Russell, II et al. | |
| 2018/0344884 A1* | 12/2018 | Kawasaki | A61L 2/087 |
| 2019/0262483 A1 | 8/2019 | Goidenko et al. | |
| 2019/0391284 A1 | 12/2019 | Fewox et al. | |
| 2020/0312476 A1 | 10/2020 | Zeevaart | |
| 2022/0208407 A1 | 6/2022 | Artman et al. | |
| 2023/0149922 A1 | 5/2023 | Thakkar et al. | |

FOREIGN PATENT DOCUMENTS

| | | |
|---|---|---|
| WO | 2022023393 A1 | 2/2022 |
| WO | 2023001764 A1 | 1/2023 |
| WO | 2023001765 A1 | 1/2023 |
| WO | 2023001767 A1 | 1/2023 |
| WO | 2023001768 A1 | 1/2023 |

* cited by examiner

ELECTRON BEAM INTEGRATION FOR STERILIZING RADIOPHARMACEUTICALS INSIDE A HOT CELL

PRIORITY CLAIM

This application is based upon and claims priority to U.S. provisional application Ser. No. 63/343,780, filed May 19, 2022, which is incorporated fully herein by reference for all purposes.

FIELD OF THE INVENTION

The present invention relates generally to sterilization systems and procedures. More particularly, the present invention relates to systems and procedures utilized during the sterilization of radioactive pharmaceuticals.

BACKGROUND OF THE INVENTION

Many products that are produced in a clean room environment are packaged for shipment and then transported to a separate area where sterilization is performed on the packaged product. Sterilization may be performed with an autoclave, an electron beam transmitter, etc., and performed in numerous locations, such as a warehouse, storeroom, etc. For example, such processes are performed on products such as, but not limited to, sterile wrappings, syringes, medical instruments, etc. However, where the product to be sterilized is intended for medical use and is radioactive, various challenges are presented.

The present invention recognizes and addresses considerations of prior art constructions and methods.

SUMMARY

One aspect of the present invention provides a sterilization system for a radiopharmaceutical product comprising a hot cell disposed within a clean room environment. A sterilization shaft extends between a first end and a second end and defines an interior. The first end of the shaft is disposed within the hot cell and the second end of the shaft is disposed externally to the clean room. An electron beam accelerator assembly is disposed within the interior of the sterilization shaft so that an emission end of the electron beam accelerator is adjacent the first end of the sterilization shaft.

According to some exemplary embodiments, a sterilization tunnel may be disposed within the hot cell adjacent the first end of the sterilization shaft. A transmission window may be positioned at the first end of the sterilization shaft so as to separate the interior of sterilization shaft from the clean room environment while allowing passage of energy from the emission end of the electronic beam accelerator. For example, the transmission window may preferably comprise titanium. The electron beam accelerator may be vertically mounted in the sterilization shaft with the sterilization tunnel being located vertically below the sterilization shaft. The electron beam accelerator assembly may be vertically removable from the interior of the sterilization shaft.

Some exemplary embodiments further include a shuttle assembly operative to move the radiopharmaceutical product into and out of the sterilization tunnel. For example, the shuttle assembly may be operative to move the radiopharmaceutical product into and out of the sterilization tunnel twice, yielding a first sweep and a second sweep. Embodiments are contemplated in which the shuttle assembly orients the radiopharmaceutical product in a first orientation during the first sweep and a second orientation during the second sweep. Preferably, the second orientation may be rotated by 180° with respect to the first orientation. In addition, the shuttle assembly may be operative to rotate automatically the radiopharmaceutical product from the first orientation to the second orientation at a time between the first sweep and the second sweep.

According to some exemplary embodiments, the shuttle assembly may be operative to separate the radiopharmaceutical product from a nest in which the radiopharmaceutical product is carried.

Another aspect of the present invention provides an electron beam sterilization system comprising an electron beam accelerator assembly having an emission end. A structure defining a sterilization zone is also provided, the sterilization zone being positioned so that energy from the emission end of the electron beam accelerator assembly will be present in the sterilization zone with the electron beam accelerator assembly is activated. A shuttle assembly is operative to move a product to be sterilized into and out of the sterilization zone in a reciprocating fashion. For example, the shuttle assembly may be operative to simultaneously move multiple units of the product to be sterilized into and out of the sterilization zone in reciprocating fashion.

According to some exemplary embodiments, the shuttle assembly is operative to separate the product to be sterilized from a nest in which the product is carried by lifting the product from the nest.

According to another aspect, the present invention provides a method of sterilizing a radiopharmaceutical product utilizing at least one electron beam accelerator assembly. One step of the method involves moving the radiopharmaceutical product in a first orientation through a first sterilization zone so as to be exposed to energy from the at least one electron beam accelerator assembly. According to another step, the radiopharmaceutical product is oriented into a second orientation different from the first orientation. A further step involves moving the radiopharmaceutical product in the second orientation through a second sterilization zone so as to be exposed to energy from the at least one electron beam accelerator assembly.

According to some exemplary methodology, the second orientation may be rotated by 180° with respect to the first orientation.

According to some exemplary methodology, the at least one electron beam accelerator comprises a single electron beam accelerator and the first sterilization zone and the second sterilization zone are a single sterilization zone. For example, the radiopharmaceutical product may be moved into and out of the single sterilization zone in reciprocating fashion twice via a first sweep and a second sweep.

According to some exemplary methodology, the radiopharmaceutical product may be separated from a nest in which it is carried (e.g., by lifting from the nest) prior to moving the radiopharmaceutical product into and out of the single sterilization zone. The radiopharmaceutical product may be placed into the nest after exposure of the radiopharmaceutical product to energy from the electron beam accelerator assembly.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
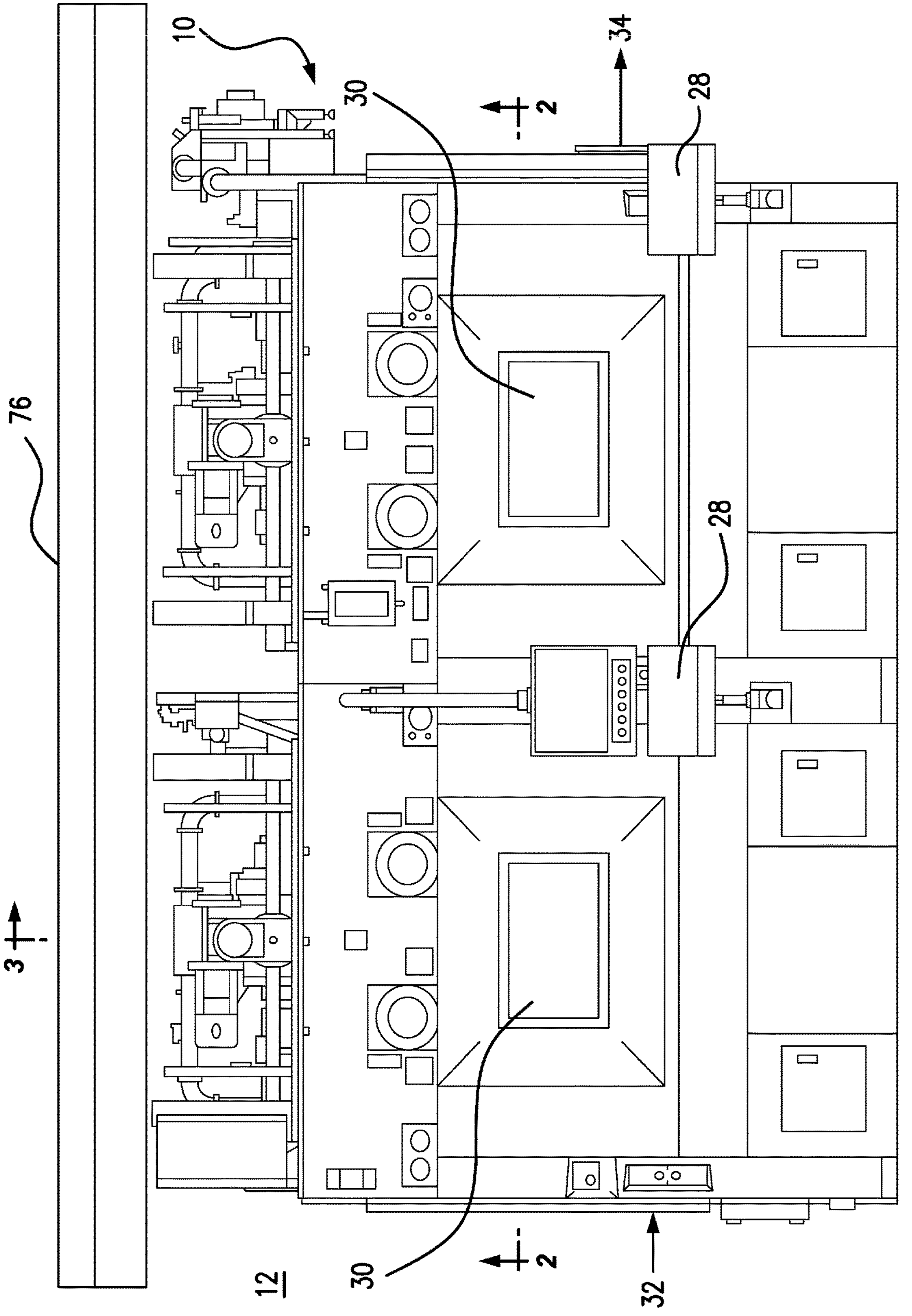
FIG. 1 is a front elevation view of a hot cell including an electron beam sterilization system in accordance with an embodiment of the present invention.

Repeat use of reference characters in the present specification and drawings is intended to represent same or analogous features or elements of the invention according to the disclosure.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 2:
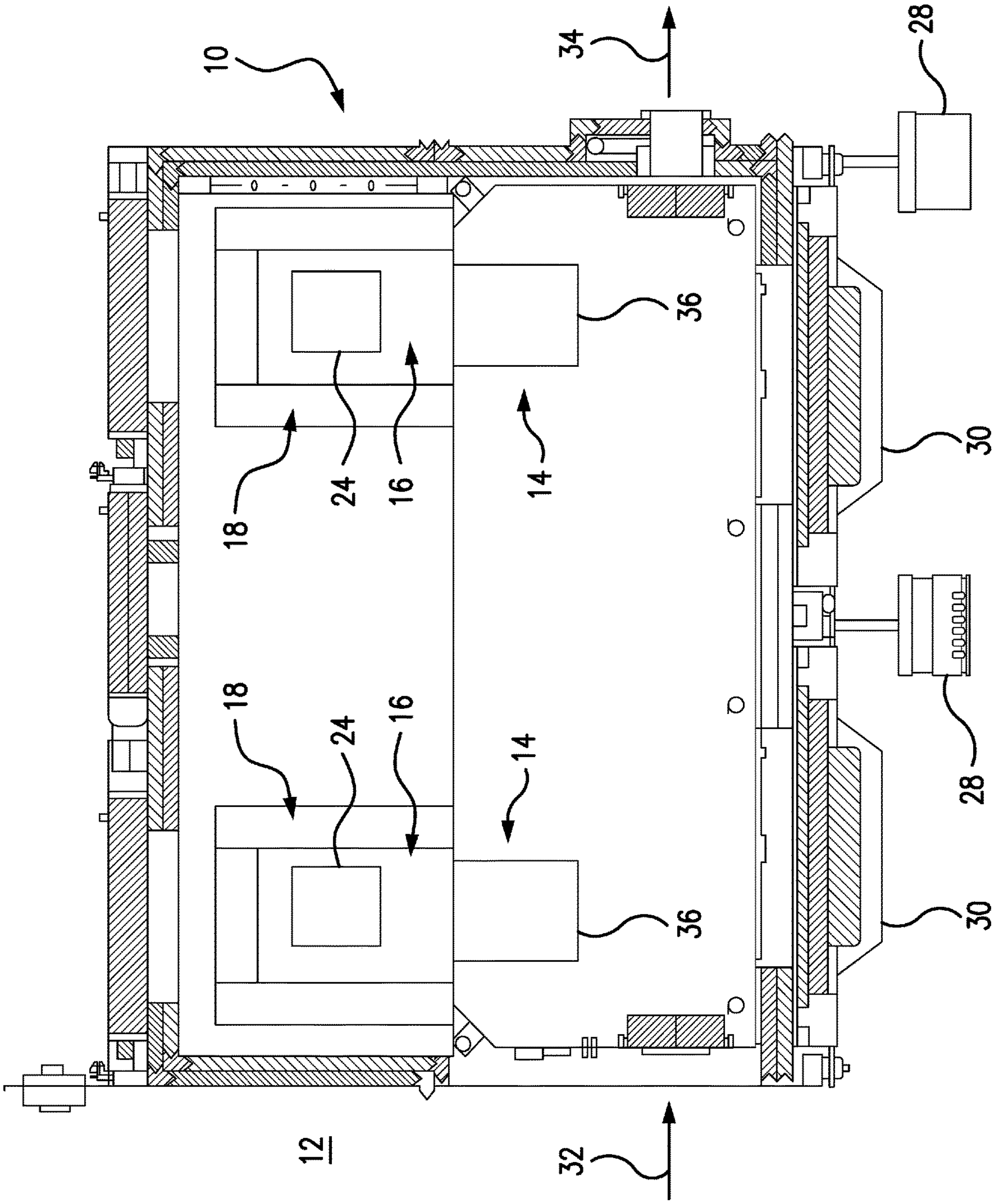
FIG. 2 is a top cross-sectional view of the hot cell shown in FIG. 1, taken along line 2-2.
Figure 3:
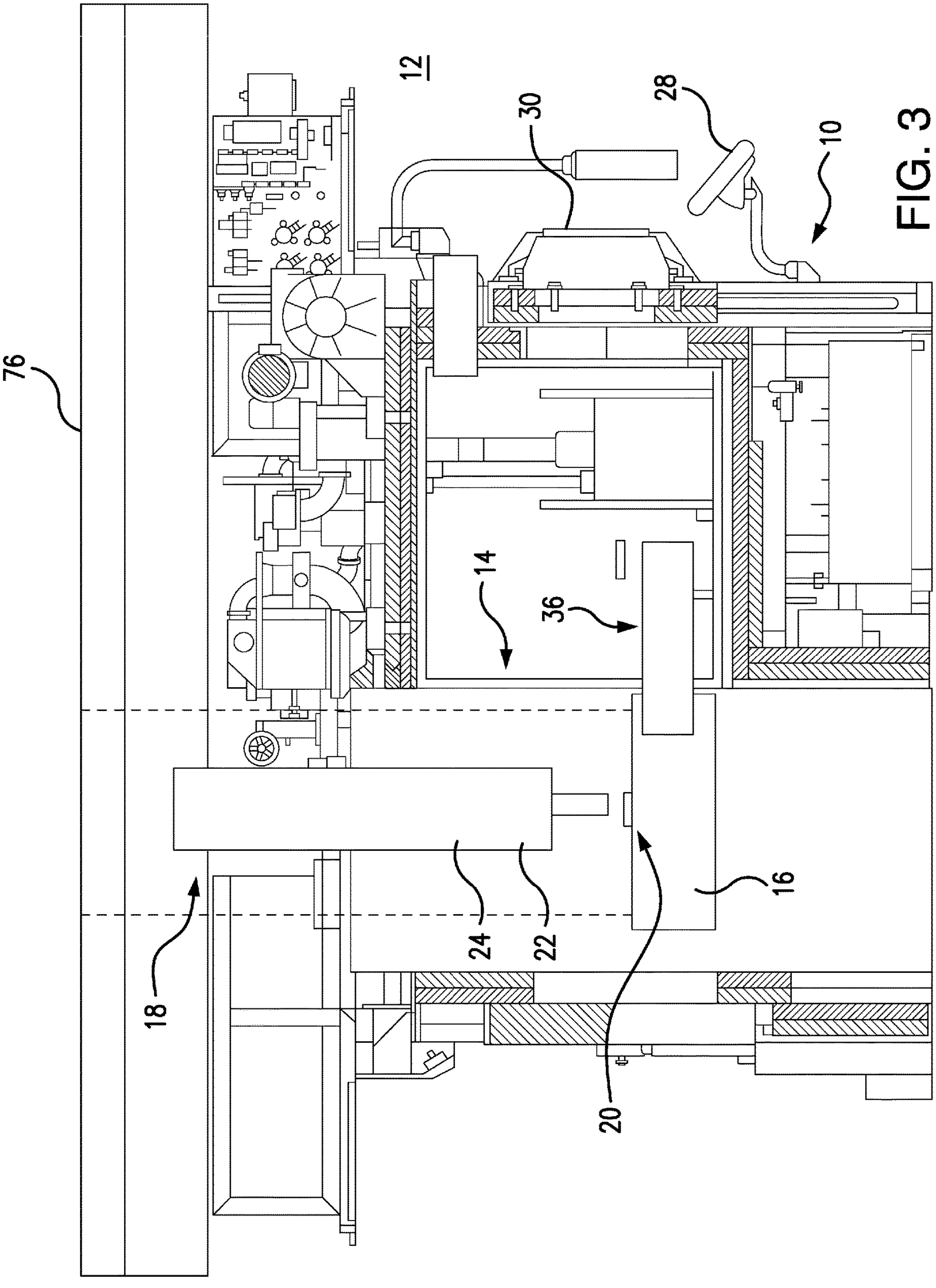
FIG. 3 is a left-side cross-sectional view of the hot cell shown in FIG. 1, taken along line 3-3.
Figure 4:
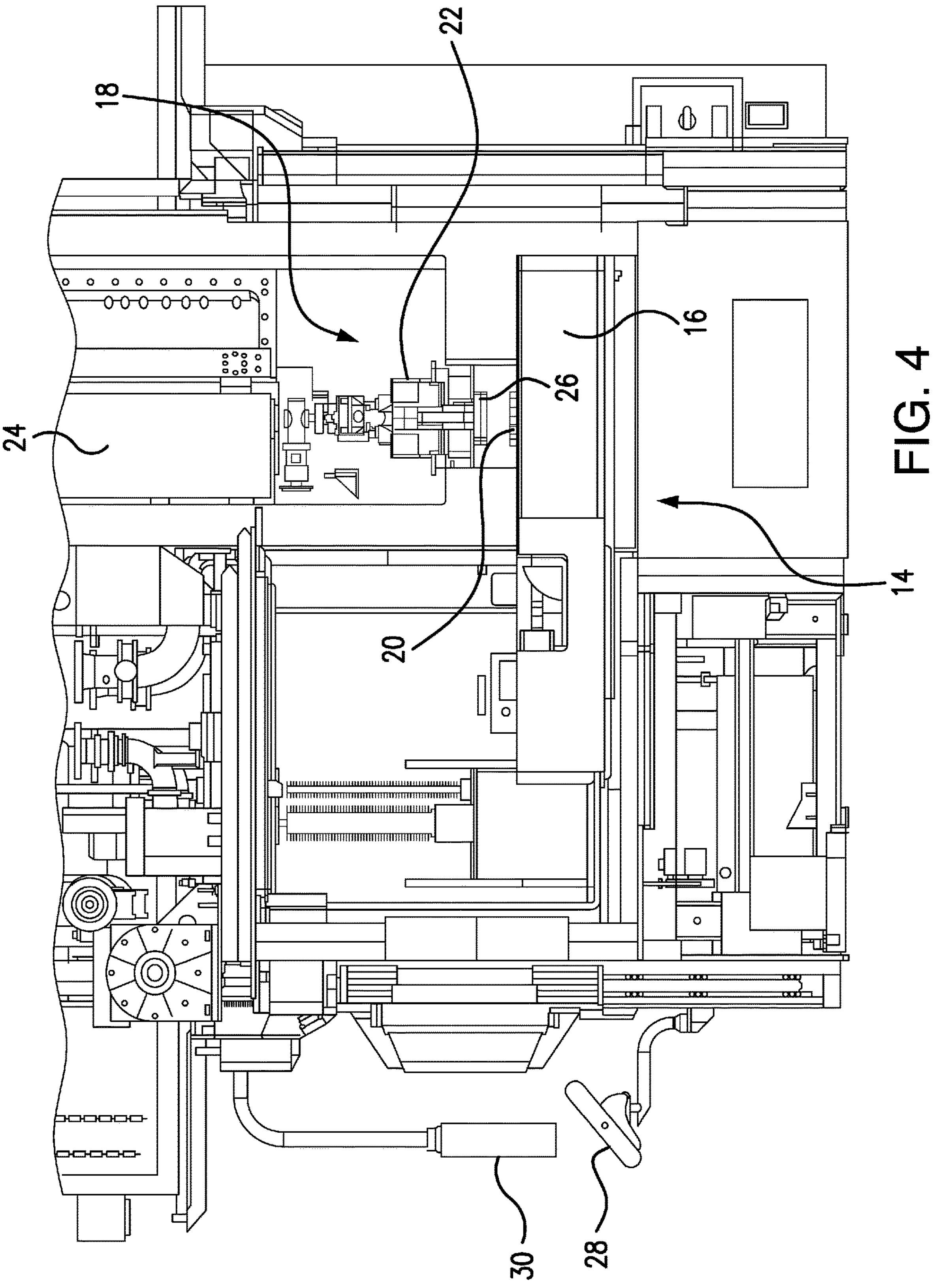
FIG. 4 is a partial cross-sectional view of the hot cell shown in FIG. 1.

As used herein, terms referring to a direction or a position relative to the orientation of the hot cell including a system for the sterilization of pharmaceuticals, such as but not limited to "vertical," "horizontal," "top," "bottom," "above," or "below," refer to directions and relative positions with respect to the hot cell's orientation in its normal intended operation, as depicted, for example, in FIGS. 1 through 3. Thus, for instance, the terms "vertical" and "top" refer to the vertical orientation and relative upper position in the perspective of FIGS. 1 through 3 and should be understood in that context, even with respect to a hot cell that may be disposed in a different orientation.

Further, the term "or" as used in this application and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used herein should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "and," and "the" may include plural references, and the meaning of "in" may include "in" and "on." The phrase "in one embodiment," as used herein, does not necessarily refer to the same embodiment, although it may.

Aspects of the present invention are especially suitable for use in the sterilization of molybdenum-99 (Mo-99) used in the production of technetium-99 m (Tc-99 m). As is known to those skilled in the art, Tc-99 m is a radioisotope that is commonly used in nuclear medicine (e.g., medical diagnostic imaging). Tc-99 m (m is metastable) is typically injected into a patient which, utilizing certain equipment, is used to image the patient's internal organs. Tc-99 m has a half-life of only about six (6) hours.

Given the short half-life of Tc-99 m, Tc-99 m is typically obtained at the location and/or time of need (e.g., at a pharmacy, hospital, etc.) via a Mo-99/Tc-99 m generator. Mo-99/Tc-99 m generators are devices used to extract the metastable isotope of technetium (i.e., Tc-99 m) from a source of decaying molybdenum-99 (Mo-99) by passing saline through the Mo-99 material. Mo-99 is unstable and decays with a 66-hour half-life to Tc-99 m. Mo-99 is typically produced in a high-flux nuclear reactor from the irradiation of highly-enriched uranium targets (93% Uranium-235) and shipped to Mo-99/Tc-99 m generator manufacturing sites. Mo-99/Tc-99 m generators are then distributed from these centralized locations to hospitals and pharmacies. Since the number of production sites is limited, compounded by the limited number of available high flux nuclear reactors, the supply of Mo-99 is susceptible to frequent interruptions and shortages resulting in delayed nuclear medicine procedures.

Mo-99 is often contained in elution columns from which it is removed via a saline solution when needed for use. Examples of elution columns that may benefit from aspects of the present invention are shown in U.S. Pat. App. Pub. No. 2022/0208407, incorporated herein by reference in its entirety for all purposes. At the time of manufacture, the elution columns themselves must be sterilized before being further packaged for shipment. Since Mo-99 has a short half-life and the number of existing production sites is limited, it is desirable to minimize the amount of time needed to reduce the irradiated Mo-99 material to a usable form. For example, a prolonged sterilization process extends far into the half-life of the Mo-99, reducing the amount of product available for ultimate use. Embodiments of the present invention desirably provide effective sterilization in a matter of minutes, e.g., two minutes.

Referring now to FIGS. 1 through 4, a hot cell 10 used in the production of radiopharmaceuticals is shown. Hot cell 10 is further disposed within a clean room environment 12 in which production occurs. In addition, the hot cell 10 includes at least one electron beam (E-beam) sterilization system 14 disposed within the hot cell 10. In this case, two such E-beam sterilization systems 14 are provided, either of which can be used to sterilize product as described more fully below. Each E-beam sterilization system 14 includes a sterilization tunnel 16 that is integrated into the liner of the hot cell 10. Tunnel 16, into which product to be sterilized is transported, is located below a sterilization shaft 18. As will be described below, shaft 18 facilitates maintenance on the components of the E-beam sterilization system 14 while eliminating impact on the clean room 12 pharmaceutical assembly area. Additionally, the disclosed configuration of the sterilization tunnel 16 facilitates cleaning of the system when necessary. In this regard, the sterilization tunnel 16, which may be installed co-planar with the floor of the hot cell 10, is preferably configured to include coved corners on all joints.

A barrier is preferably provided to separate the clean room 12 environment from the sterilization shaft 18. In this case, the barrier is configured as a sealed titanium transmission window 20, such that the electron flux of the E-beam accelerator's scan horn 22 is reliably transmitted into the tunnel 16 to impinge the radiopharmaceutical product therein. The transmission window 20 is hermetically sealed from the interior of the hot cell 10 so that the environment of the hot cell 10 and, therefore, clean room 12 are not breached when opening the sterilization shaft 18 in which the E-beam accelerator 24 (and its scan horn 22) are disposed. The transmission window 20 is the primary environmental seal for the hot cell grade environment (Class 100, 000 or ISO 8/EV Grade C). The transmission window 20 may be very thin (e.g., 0.002 inches) and comprise titanium. Note, the emission end of the E-beam accelerator 24 also preferably includes a transmission window 26 constructed similarly to window 20. The sterilization tunnel 16 preferably has connections for vaporized hydrogen peroxide (VHP) sterilization. In addition, the hot cell 10 primary ventilation system is preferably connected to the sterilization tunnel 16 to draw air from the hot cell 10 for venting both heat and E-beam generated ozone.

As noted above, the hot cell in this embodiment includes a pair of E-beam sterilization systems 14 that are side-by-side, allowing each sterilization system to be independently operated. In this regard, an operator utilizing one of the control panels 28 while viewing operations through a corresponding window 30 may operate an associated one of the E-beam sterilization systems 14. Preferably, the radiopharmaceutical product to be sterilized enters the hot cell 10 from a previous manufacturing step through an entrance portal 32 on the left side of the hot cell 10 and exits the hot cell 10 through an exit portal 34 on the right side of the hot cell 10 after the sterilization process.

Figure 5:
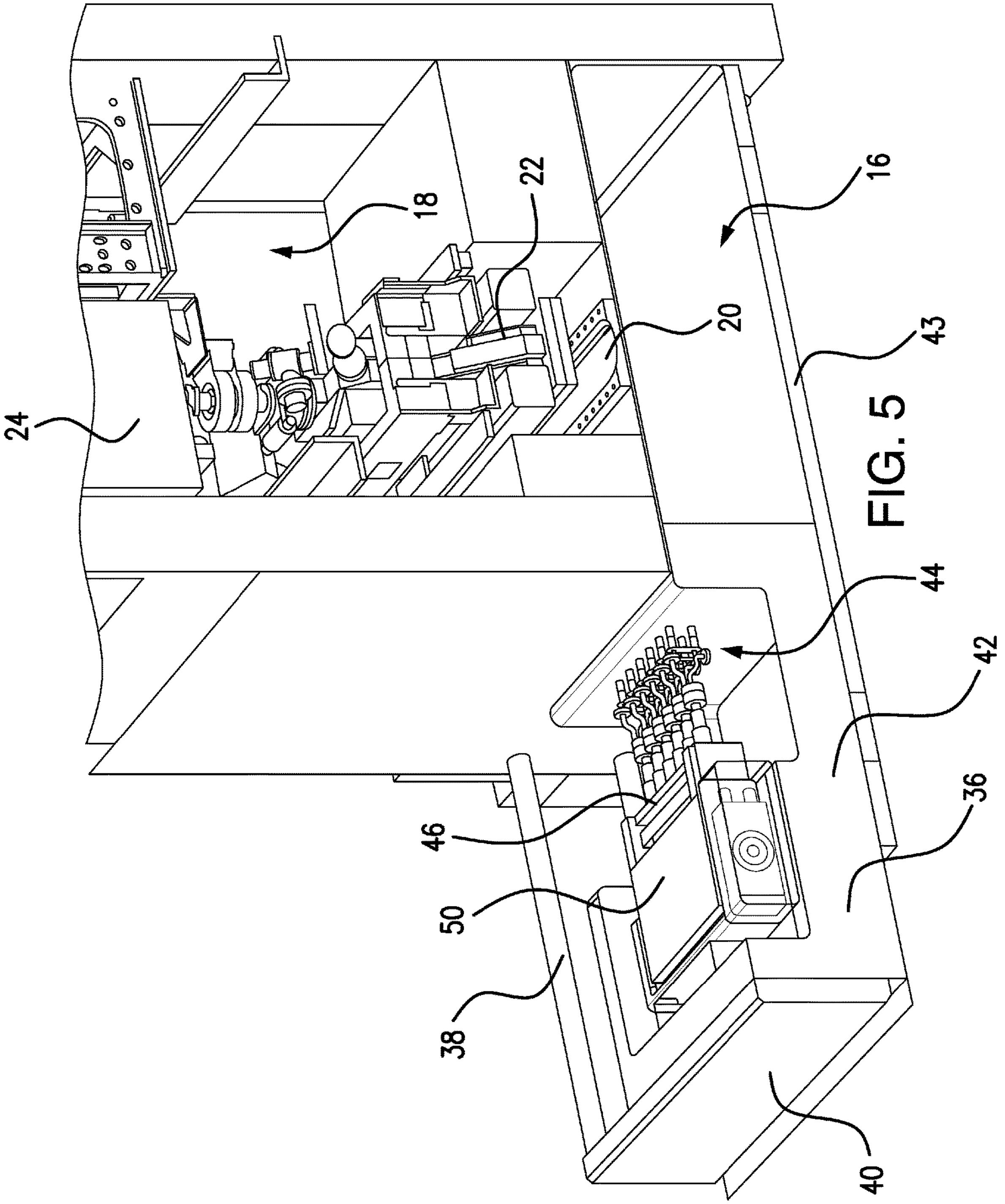
FIG. 5 is a partial cross-sectional isometric view of the sterilization tunnel and shuttle assembly of the hot cell shown in FIG. 1.

Referring now also to FIG. 5, sterilization tunnel 16 includes a shuttle assembly 36 operative to, among other things, move the product to be sterilized into and out of the tunnel 16 such that it passes through the beam emitted by scan horn 22. In the illustrated embodiment, shuttle assembly 36 is actuated by a pair of servo-driven rod linear actuators 38 positioned on each lateral side. Preferably, the rod actuators 38 are sealed to the liner of the hot cell 10 using radiologically-tolerant seal systems to ensure cleanability and air tightness. As shown, the rod actuators 38 are attached in this case to a removable front plate assembly 40, allowing for the removal of the entire shielded shuttle ("slider") 42. (In alternate embodiments, rather than the disclosed rod linear actuators 38, an alternate linear transfer device, such as rollers, chain drives, rails, etc., may be used to support and move the shielded shuttle.) Removal of the shuttle 42 allows easy access to the sterilization tunnel 16 for both cleaning and inspection. A plate 43, e.g., an aluminum plate of sufficient thickness, is located at the bottom of tunnel 16 to stop further travel of the electron beam.

As will be described below, the shuttle 42 includes mechanisms to manipulate and position the product for sterilization. While various suitable mechanisms for accomplishing such manipulation are contemplated, some embodiments of the invention utilize pneumatic mechanisms. The shuttle 42 is also preferably internally cooled by water to prevent over-heating. The front plate assembly 40 may include seals for transmitting pneumatic fluid, electrical signals, and water cooling to the shuttle assembly. It will be appreciated that the shuttle 42 prevents excess radiation from reaching the operators of the hot cell 10 during the sterilization process.

Figure 6A:
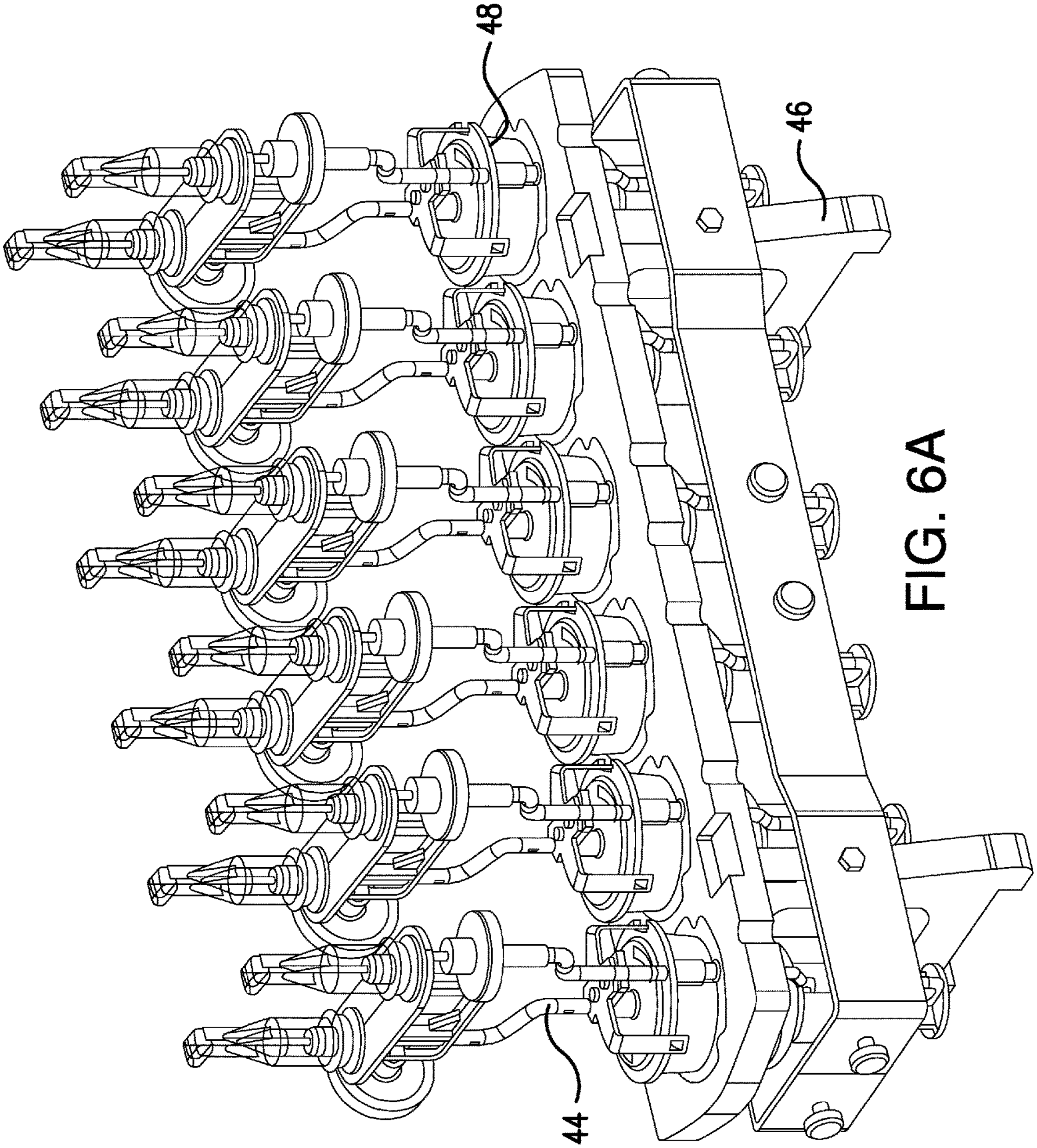
FIG. 6A is a perspective view of a nest device that carries a radioactive pharmaceutical product through manufacturing steps with six of the products carried thereby.
Figure 6B:
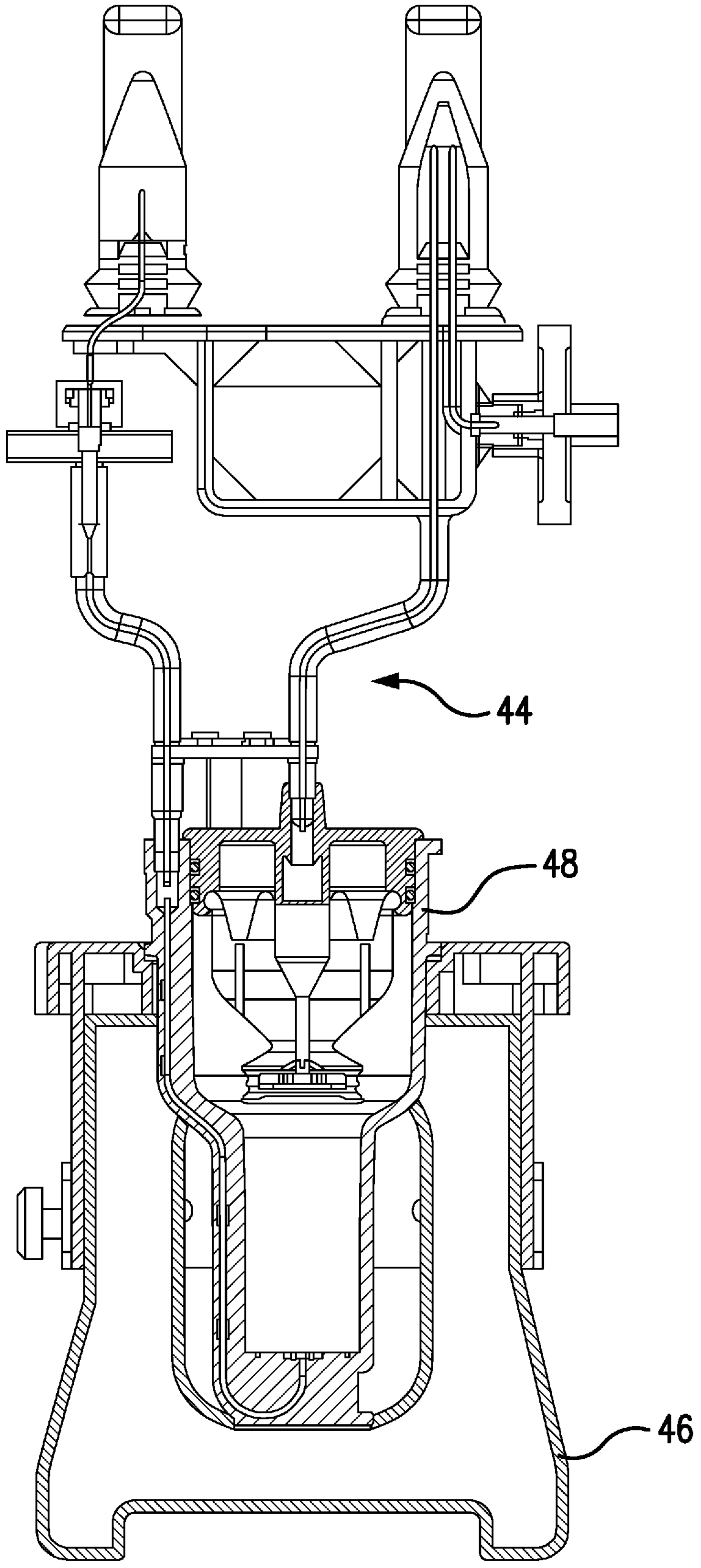
FIG. 6B is a cross-sectional view of the nest device of FIG. 6A.

Referring now also to FIGS. 6A and 6B, the radiopharmaceutical product 44 to be sterilized (e.g., elution column) is typically received into the hot cell in groups (e.g., groups of six) carried vertically by a nest 46. In this regard, nest 46 defines holes in which a column portion 48 of the product 44 is received. Shuttle 42 preferably includes a lifter assembly 50 which is operative to remove the product 44 from the nest 46 before the product is passed into and out of the tunnel 16 so that the nest 46 will not attenuate the energy of the electron beam emitted from the horn 22. In addition, removal of the product 44 from the nest 46 prior to sterilization should increase the service life of the nest 46 due to absence of electron beam exposure. As will be described, lifter assembly 50 also preferably rotates the product 44 so that it can be reintroduced to the tunnel 16 in order to ensure that both sides of the product 44 are introduced to the flux.

Figure 7A:
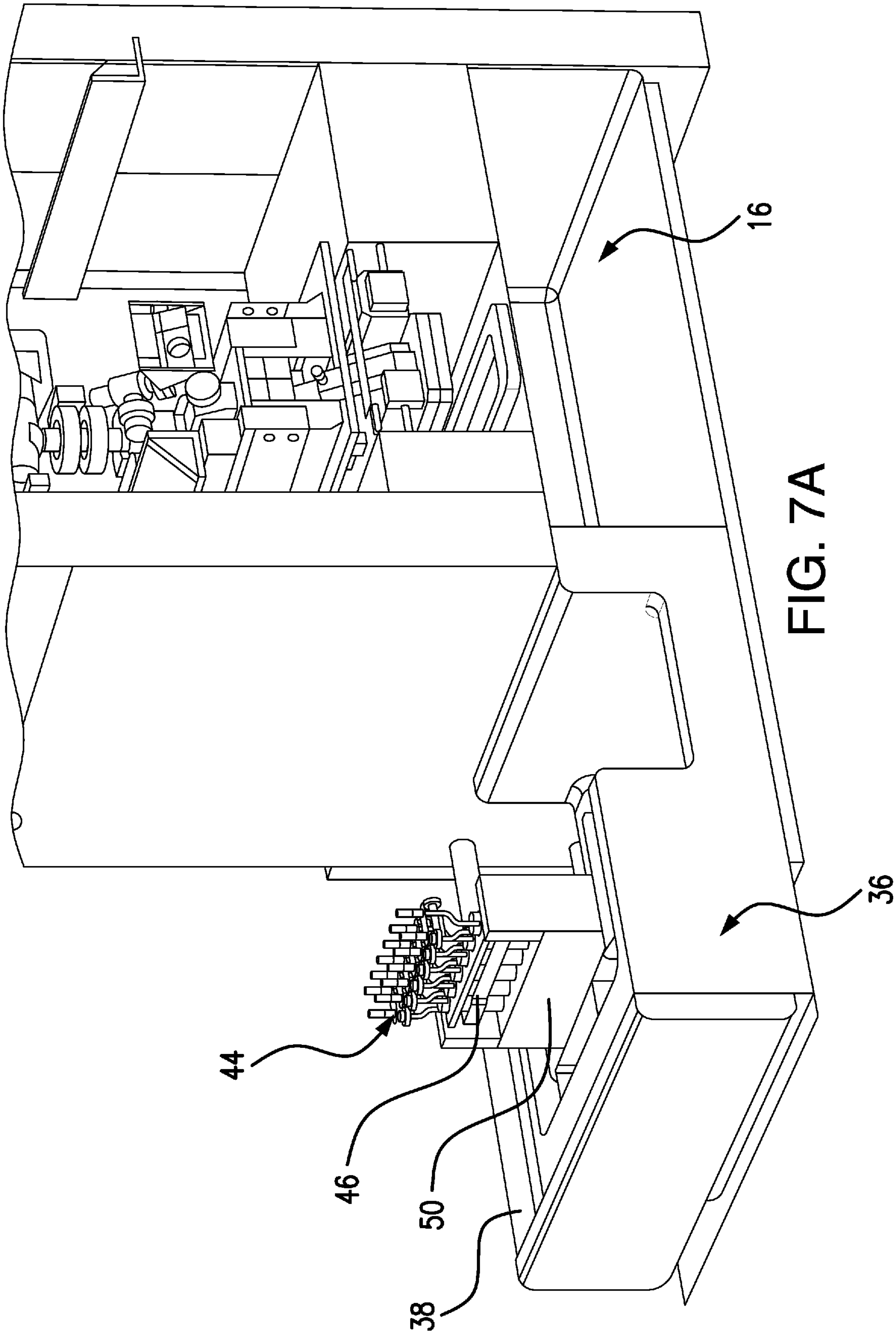
FIGS. 7A through 7K are views similar to FIG. 5 but showing a sterilization sequence in accordance with certain aspects of the present invention.
Figure 7B:
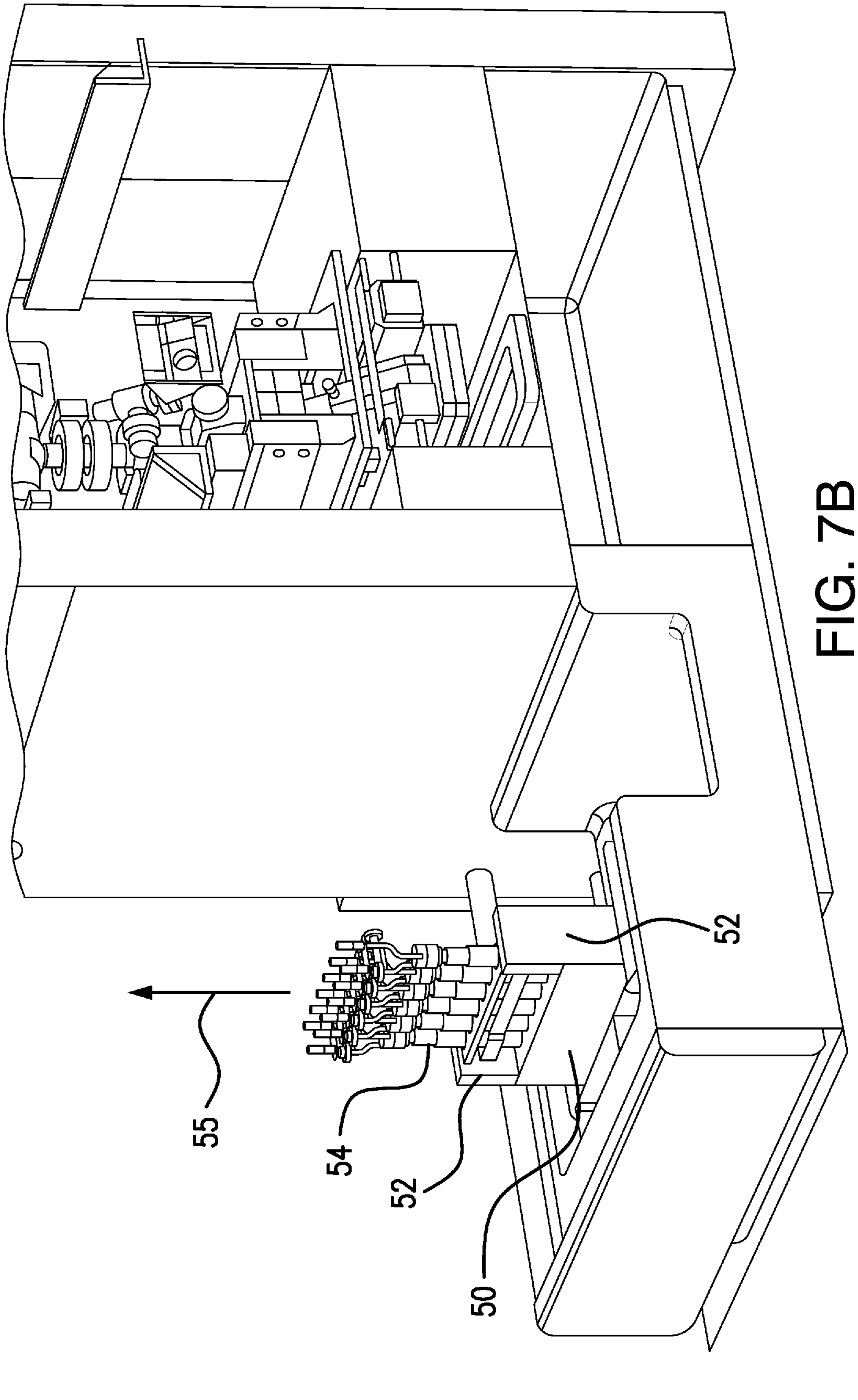

Operation of the shuttle assembly 36 will be further described with reference to FIGS. 7A through 7K. As shown in FIG. 7A, nest 46, carrying multiple products 44 to be sterilized, is placed in lifter assembly 50. As can be seen, lifter assembly 50 is rotated up to a vertical orientation for receipt of nest 46. As shown in FIG. 7B, clamps 52, initially open to allow insertion of the nest 46, then move inward so as to grip the nest 46. Product lifters (such as the one indicated at 54), then move from a retracted to an extended position so as to lift the products 44 away from the nest 46 (as indicated by arrow 55). Referring now briefly to FIG. 8, the product lifters 54 may have an extensible rod 56 carrying a flexible cup 58 at its distal end that gently engages the column portion 48 of the product 44. In this case, rod 58 is attached to a piston 60 at its opposite end that reciprocates in a pneumatic cylinder 62.

Figure 7C:
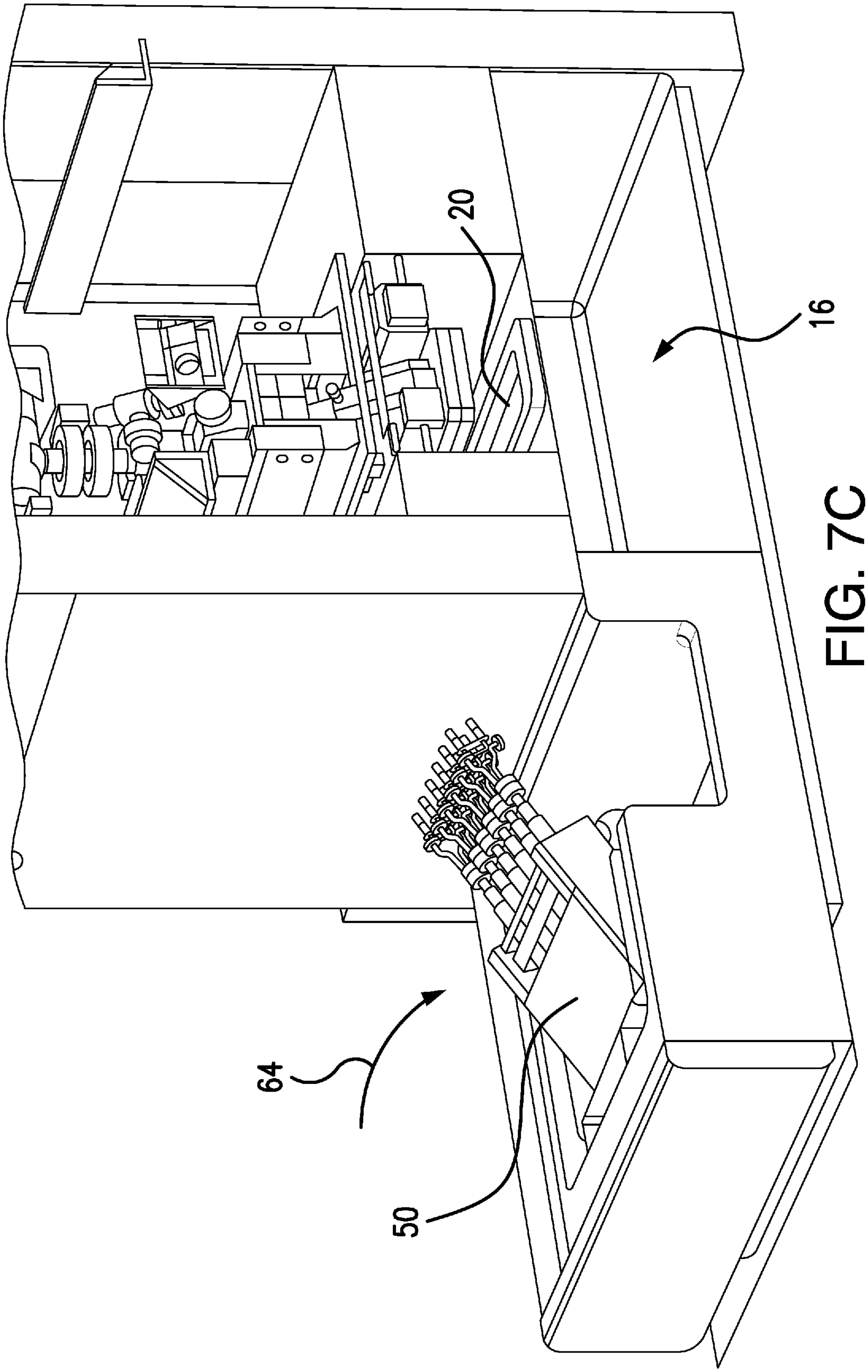
Figure 7D:
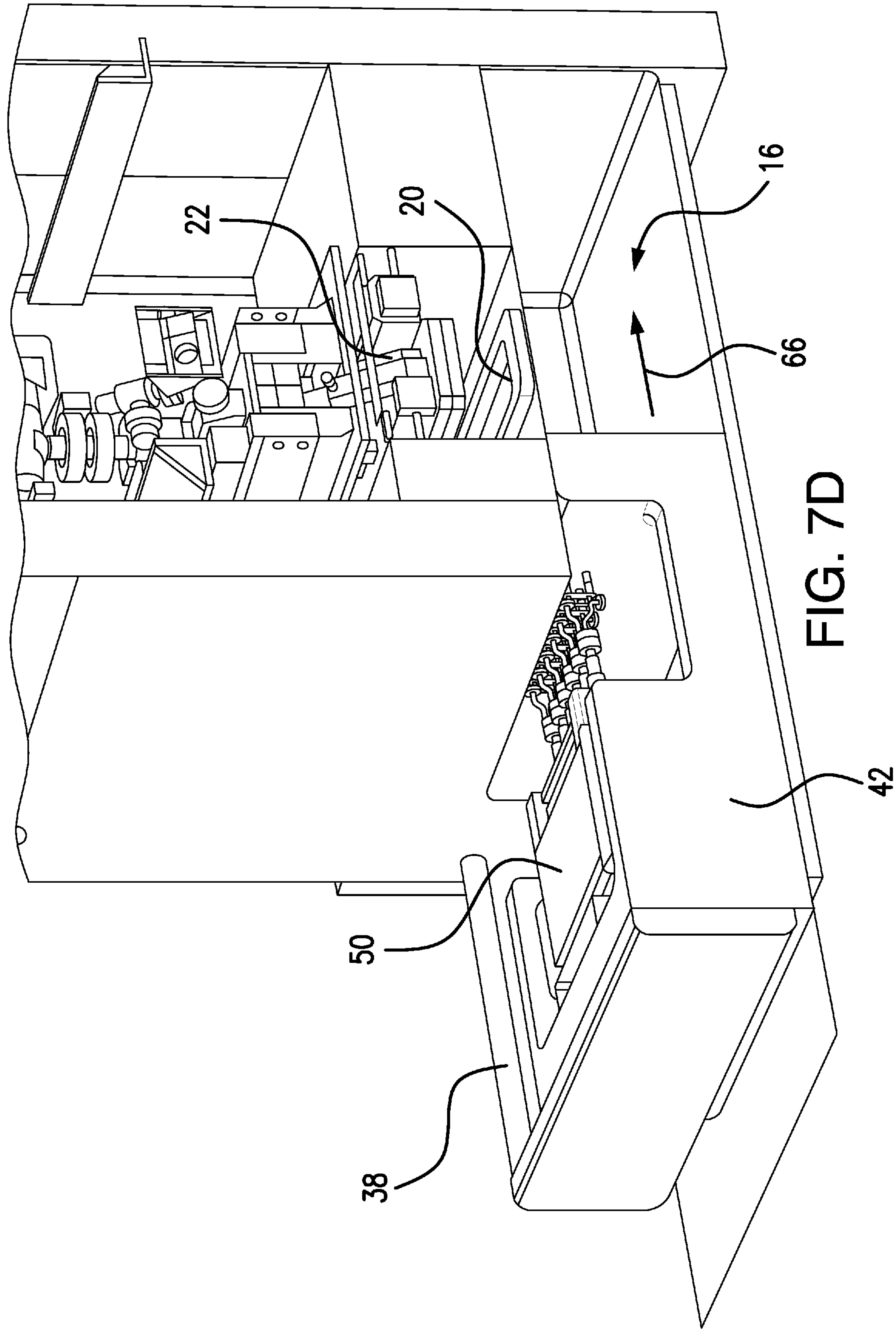
Figure 7E:
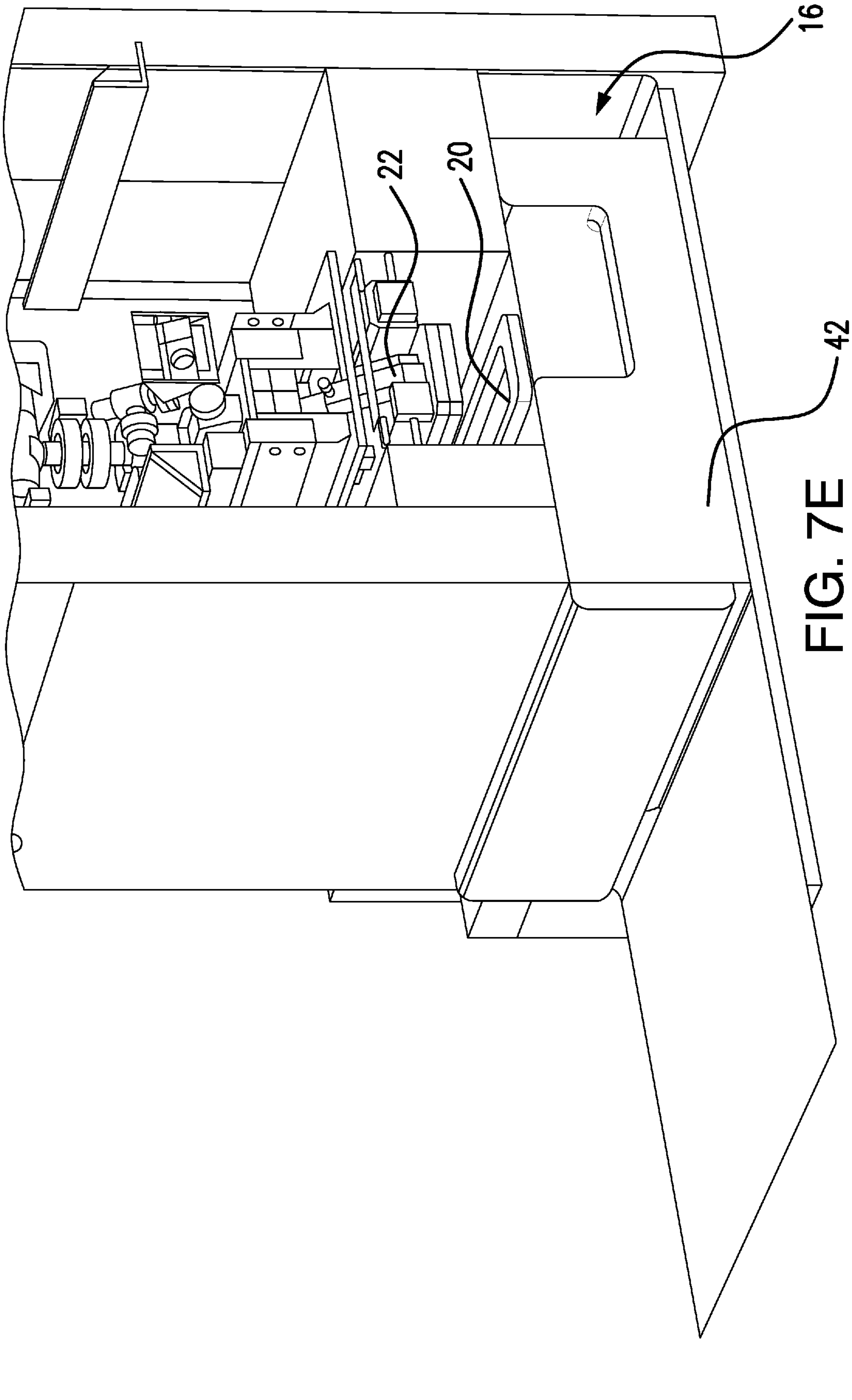
Figure 7F:
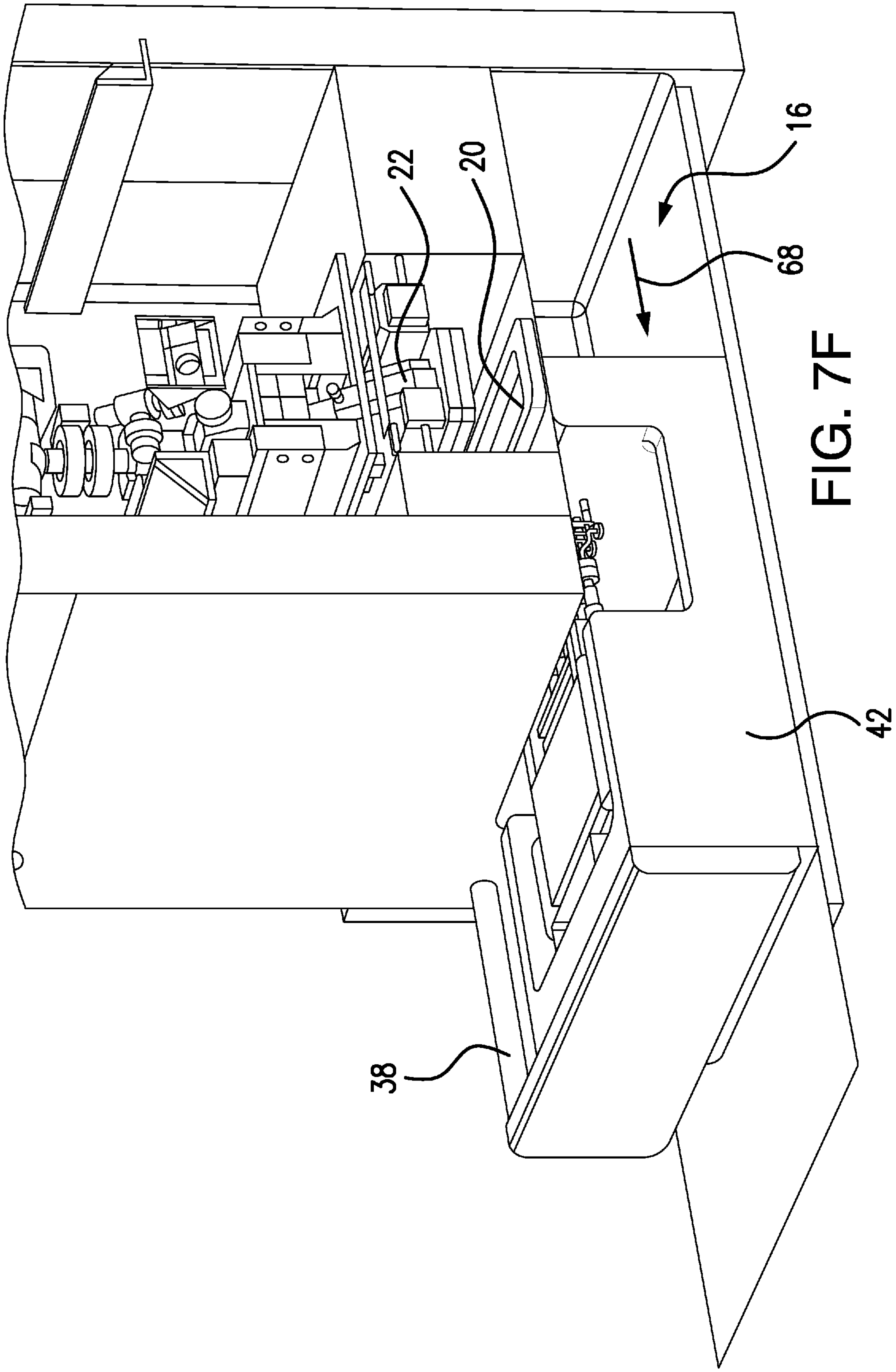
Figure 8:
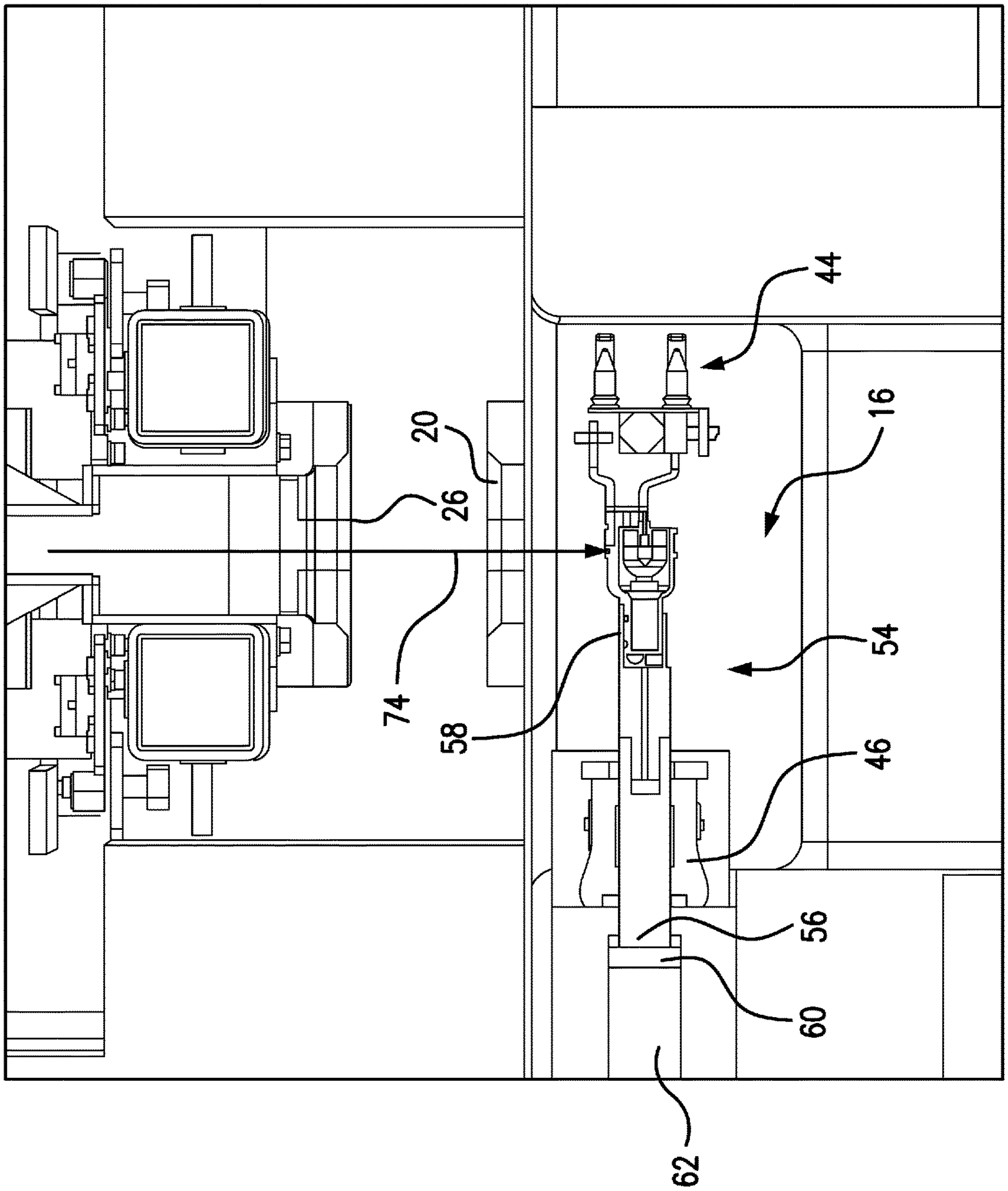
FIG. 8 is a partial cross-sectional view of the sterilization tunnel of the hot cell shown in FIG. 1 diagrammatically illustrating sterilization of the product.

Referring now to FIG. 7C, lifter assembly 50 then rotates (as indicated by arrow 64) until products 44 are oriented horizontally. As shown in FIGS. 7D through 7F, shuttle 42 then moves into (as indicated by arrow 66) and out of (as indicated by arrow 68) the tunnel 16 due to the action of actuators 38. As a result, the side of product 44 that is facing up will pass under window 20 coming and going. Preferably, the product group may be rotated slightly about the shuttle axis as it is moved in and out (i.e., a "roll") so as to enhance unform exposure to the flux field.

Figure 7G:
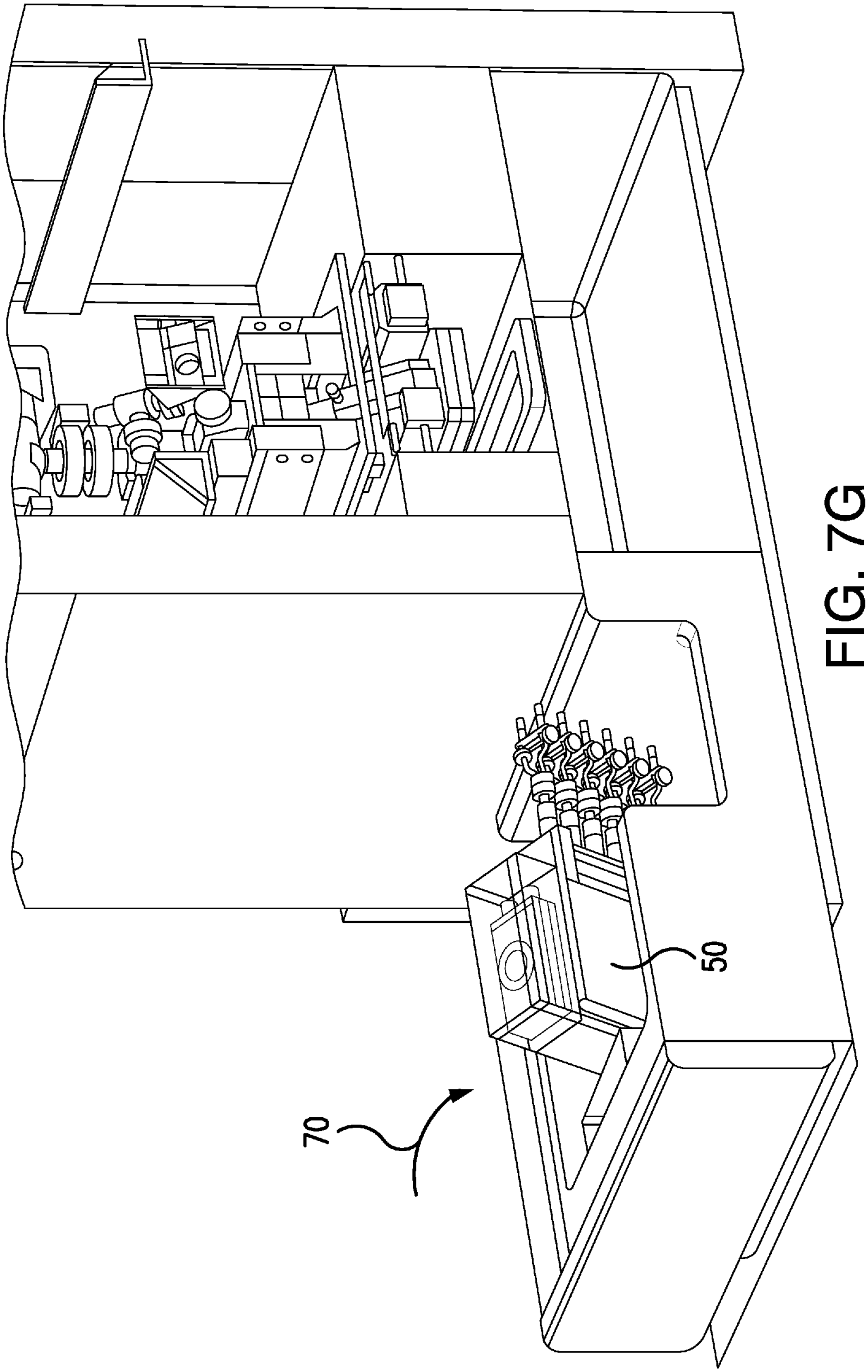
Figure 7H:
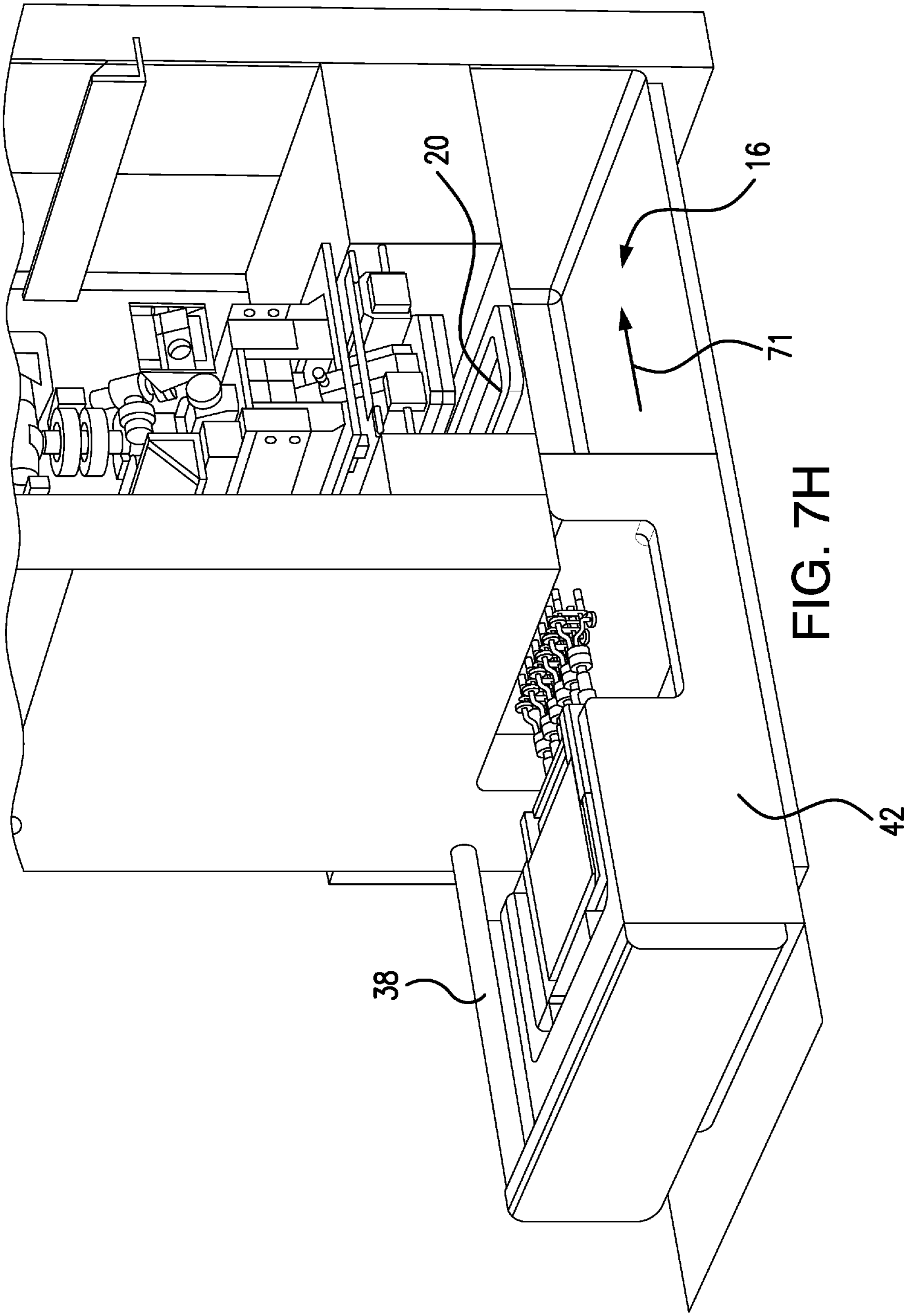
Figure 7I:
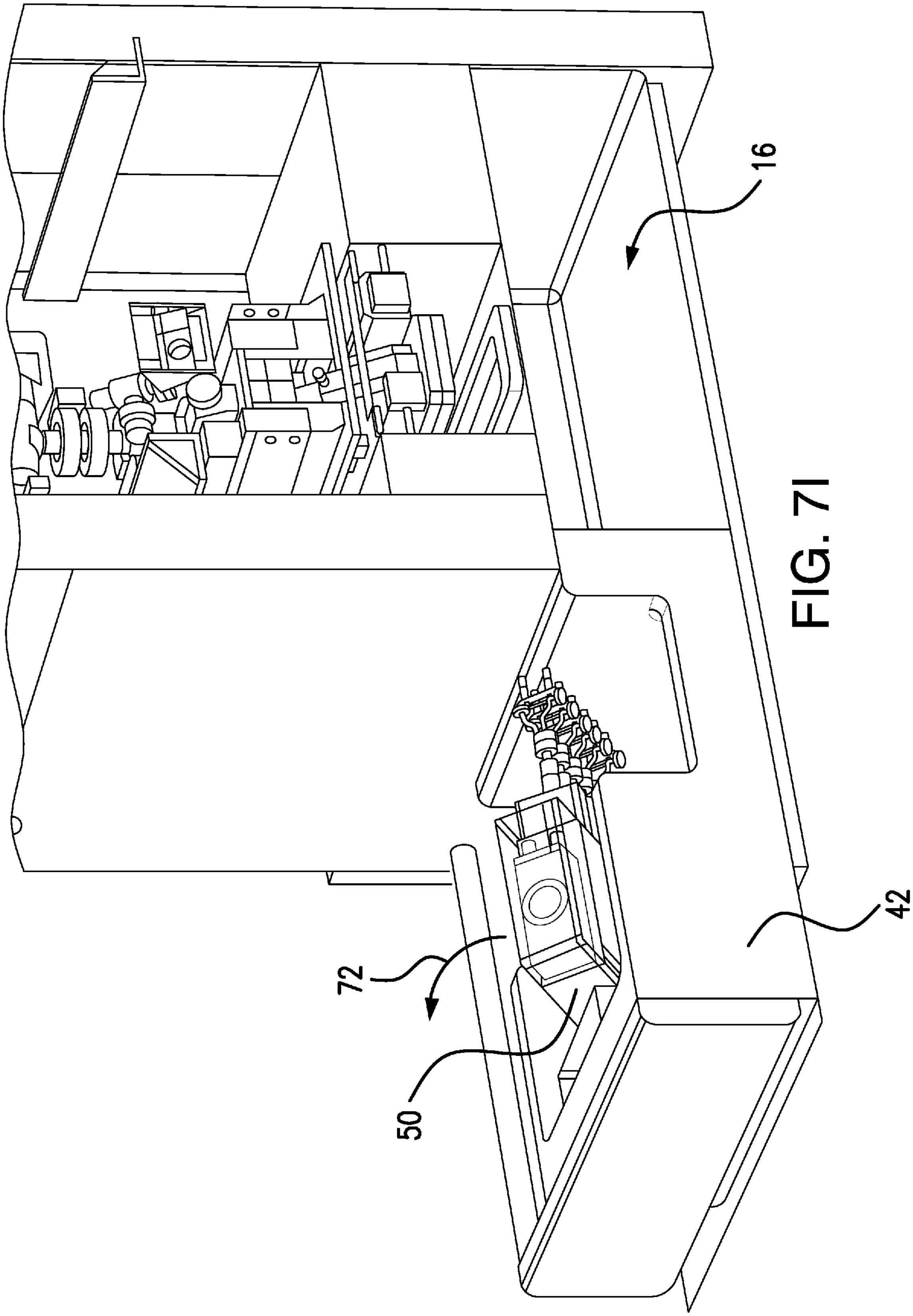
Figure 7J:
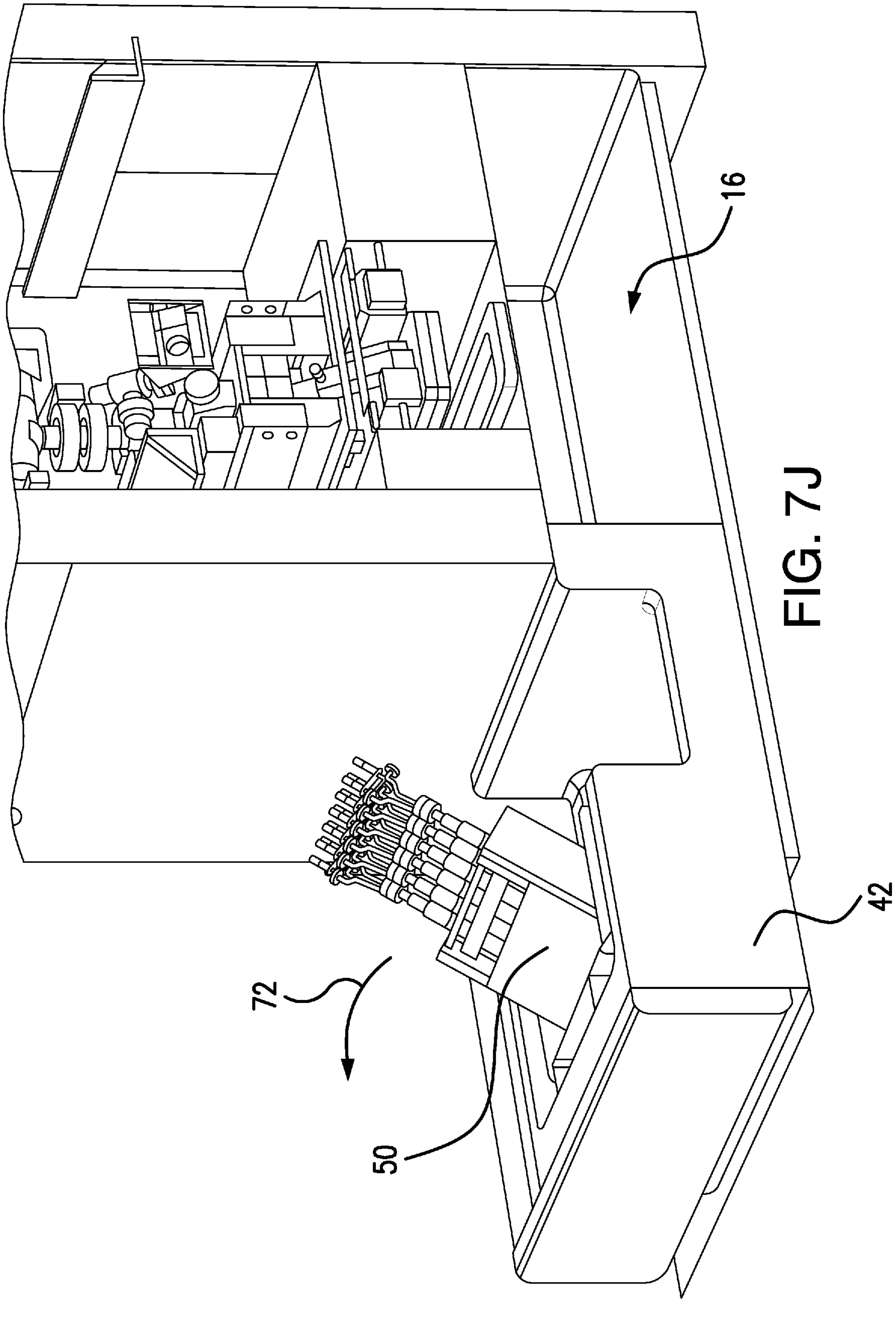
Figure 7K:
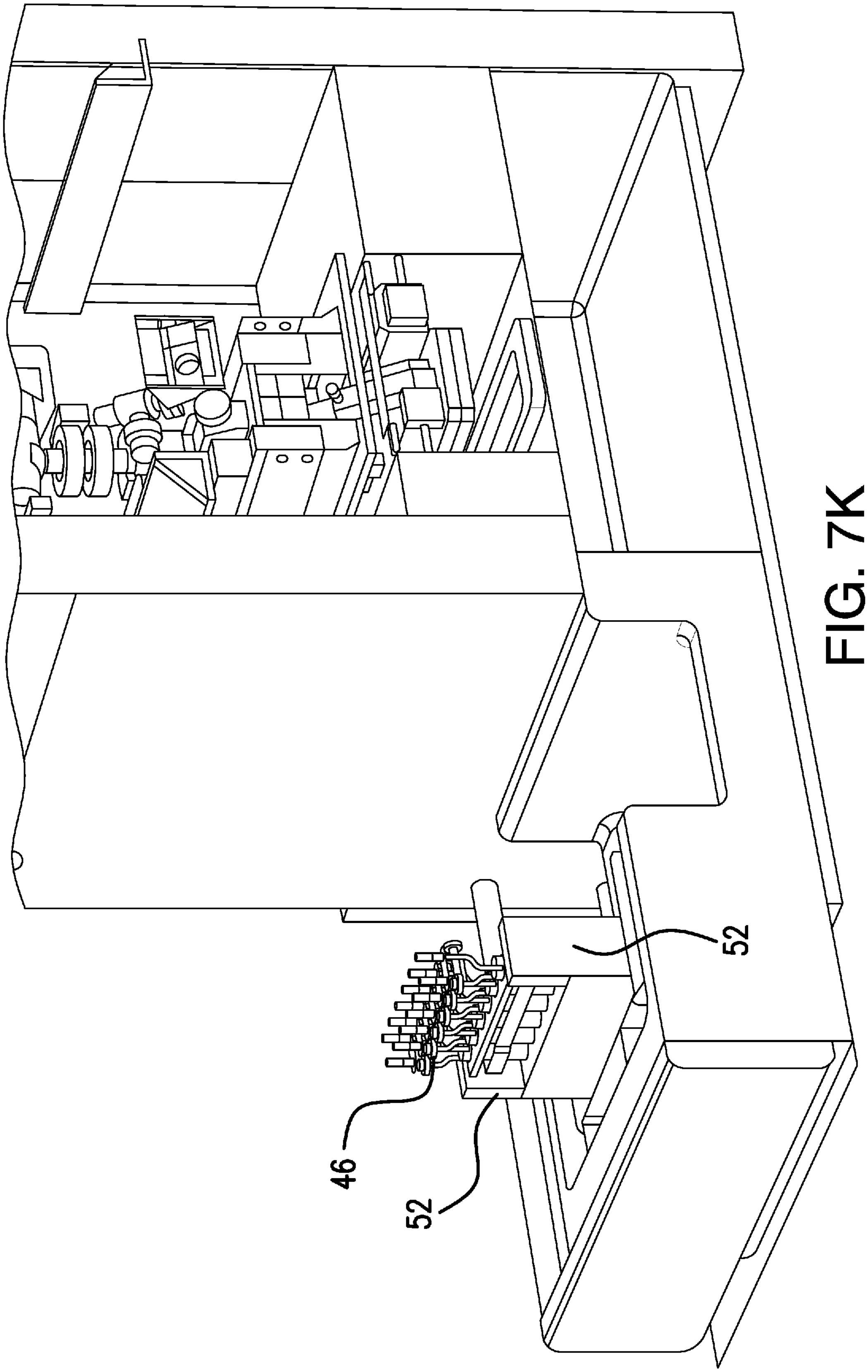

As shown in FIG. 7G, lifter assembly 50 then rotates the group of products 44 by 180° (as indicated by arrow 70) so that the side that was previously facing down will be facing up. As shown in FIG. 7H, shuttle 42 is then moved in and out of the tunnel 16 in a manner similar to the first pass (as indicated by arrow 71). Referring now to FIG. 7I, lifter assembly 50 then rotates the group of products by 180° (as indicated by arrow 72) so that the side initially facing up will be so again. Next, as shown in FIG. 7J, lifter assembly 50 is rotated back to vertical (as indicated by arrow 73). As shown in FIG. 7K, the products 44 are then lowered back into nest 46 and clamps 52 are retracted. At this point, with both sides of the product exposed twice, sterilization is complete and nest 46 can then be passed to the next phase of the manufacturing process.

Figure 9:
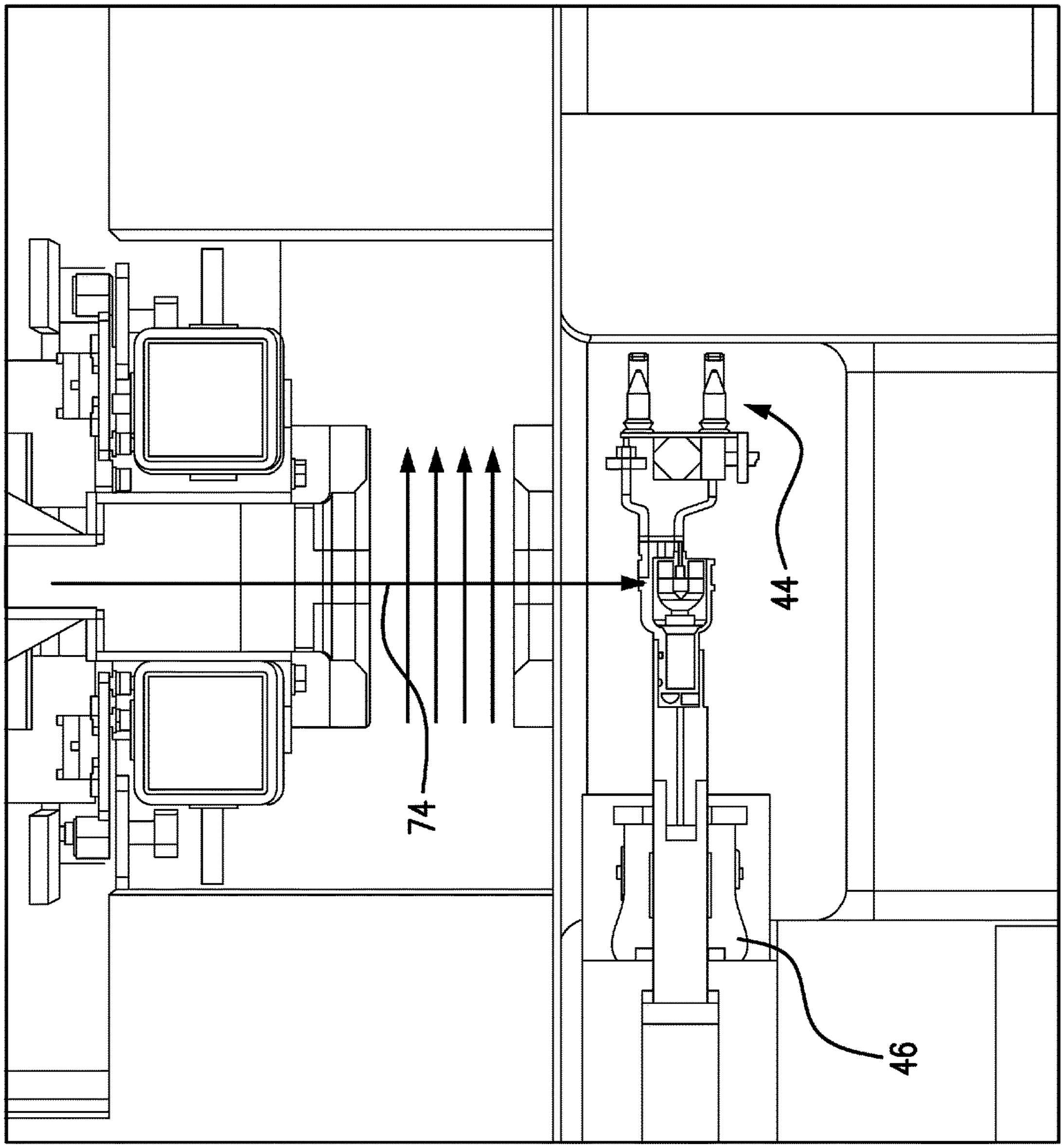
FIG. 9 is a view similar to FIG. 8 but also showing cooling of windows through which electron beam passes.

FIGS. 8 and 9 show the electron beam flux 74 passing through window 20 so as to impinge product 44 as it passes into and out of the tunnel 16. Note that the nest 46 will not pass through the flux line because of the operation of lifter assembly 50 as described above. To maintain optimal service life, the titanium transmission windows 20 and 26 on the top wall of the sterilization tunnel 16 and the emission end of the E-beam accelerator 24, respectively, both require cooling. Such cooling may be achieved in multiple ways, including: a water-cooled heat exchanger with a blower fan and duct system that is attached to the E-beam accelerator 24; a cold air vent duct in the sterilization tunnel 16 with a duct that directs the cool air flow to the windows 20 and 26, with the sterilization tunnel 16 attached to nuclear ventilation; and water-cooling configurations are also possible.

Figure 10A:
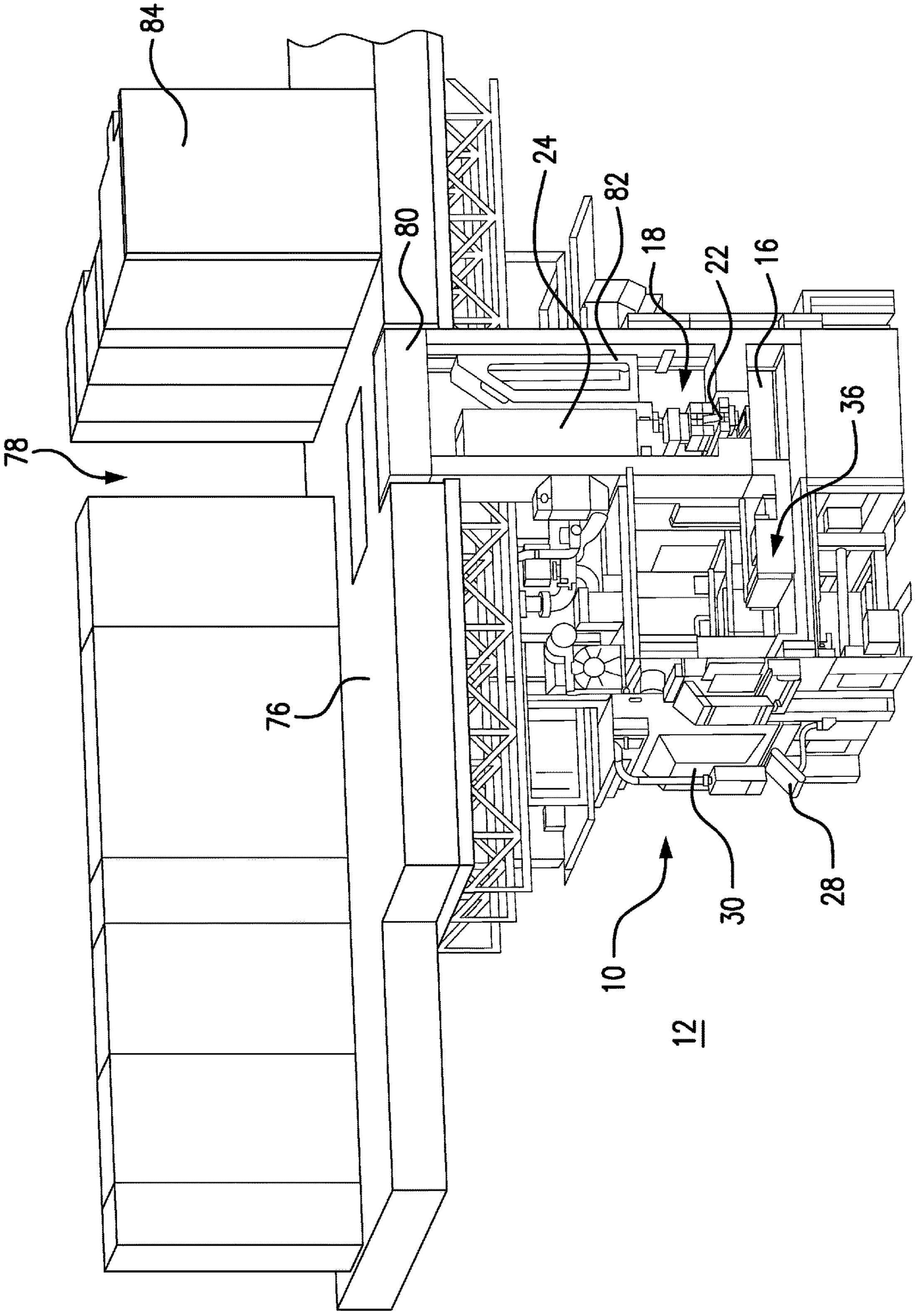
FIGS. 10A and 10B are perspective cross-sectional views of the hot cell shown in FIG. 1 and other contiguous structure.
Figure 10B:
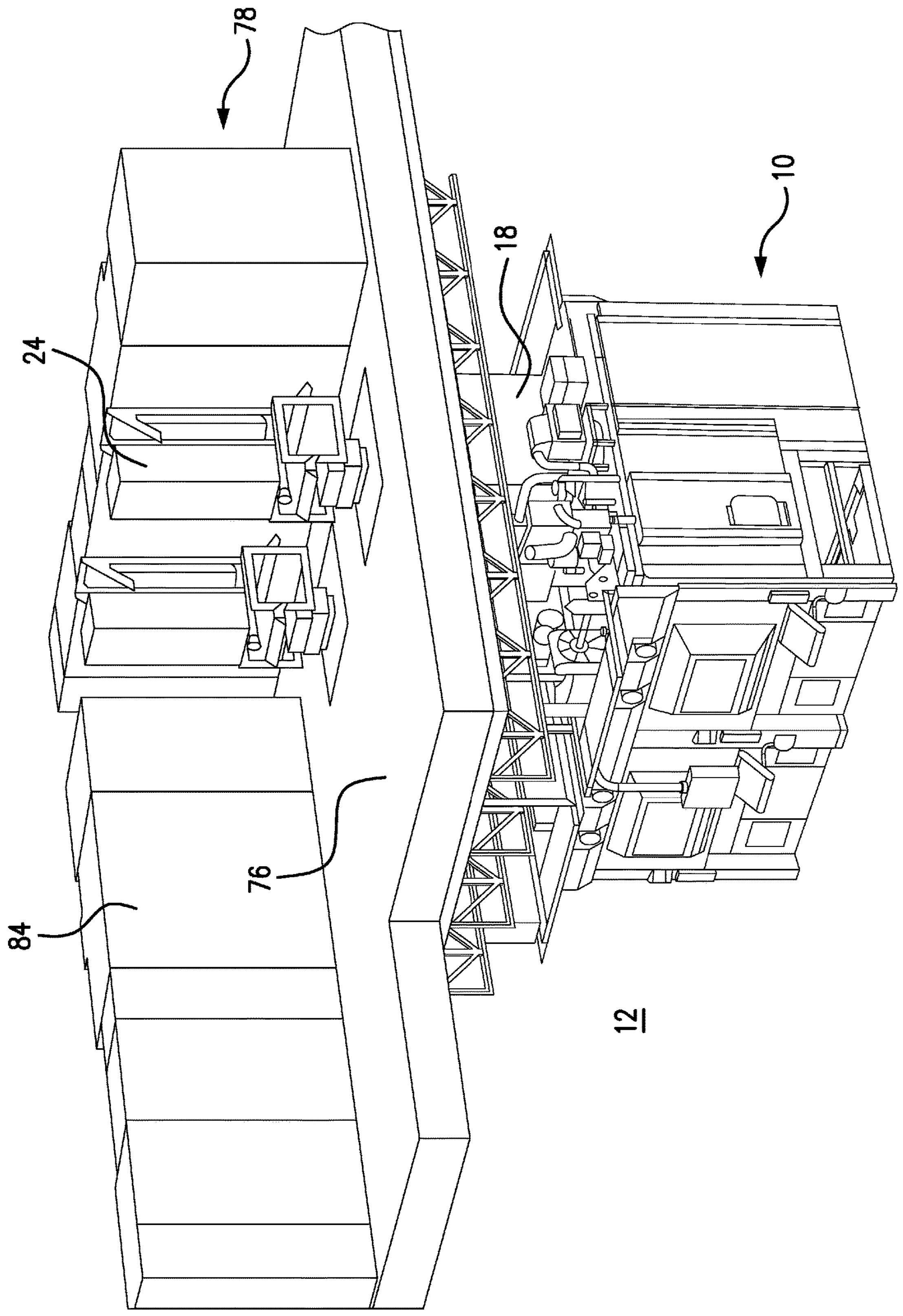

Referring now to FIGS. 10A and 10B, the electron beam accelerator 24 is installed in the sterilization shaft 18 as noted above. Sterilization shaft 18 extends vertically so that it can be accessed via the floor 76 of the room 78 above hot cell 10. Preferably, shaft 18 may be stainless steel-clad tungsten shielded and sealed on the top and bottom to maintain a redundant isolation barrier between the environment of the clean room 12 and the maintenance area that includes both the sterilization shaft 18 and the room 78. With the removal of the sealed top-mounted shielded plug 80, the accelerator 24 (with scan horn 22) may be extracted upwardly from the sterilization shaft 18 for routine maintenance, as shown in FIG. 10B. Guiding rails 82 may be mounted to the sterilization shaft 18 wall to aid in the accurate installation and removal of the E-beam accelerator assembly. Preferably, these guiding rails 82 taper inwardly and are fitted within an end stop near the inserted operating position of the accelerator 24 for repeatable, rapid installation. The sterilization shaft 18 preferably maintains an energy chain supplying power, electronics connections, and cooling water to the E-beam accelerator 24 when in the lifted position so that maintenance activities on the accelerator 24 may continue with the accelerator 24 in the retracted position.

As shown, various control cabinets 84 are located in the room 78 to allow for electrical access external to the clean room 12. The configuration of the sterilization tunnel 18 extending downwardly into the hot cell 10 (and thus the environment of clean room 12) allows for two to three hour maintenance windows without compromising the hot cell 10 and clean room 12 environments below since the sterilization shaft 18 is sealed and there is no air exchange between the sterilization shaft 18 and the clean room 12 on the bottom floor. Preferably, positive pressure is maintained in clean room 12 relative to shaft 18 so that any breach (such as a crack in window 20) will not cause flow of air into clean room 12. Instead, air would flow into shaft 18 from clean room 12. Maintaining power connections to the accelerator 24 in the lifted position allows it to be electrically tested at the same time the cleaning operations of the sterilization shaft 18 is performed.

Figure 11:
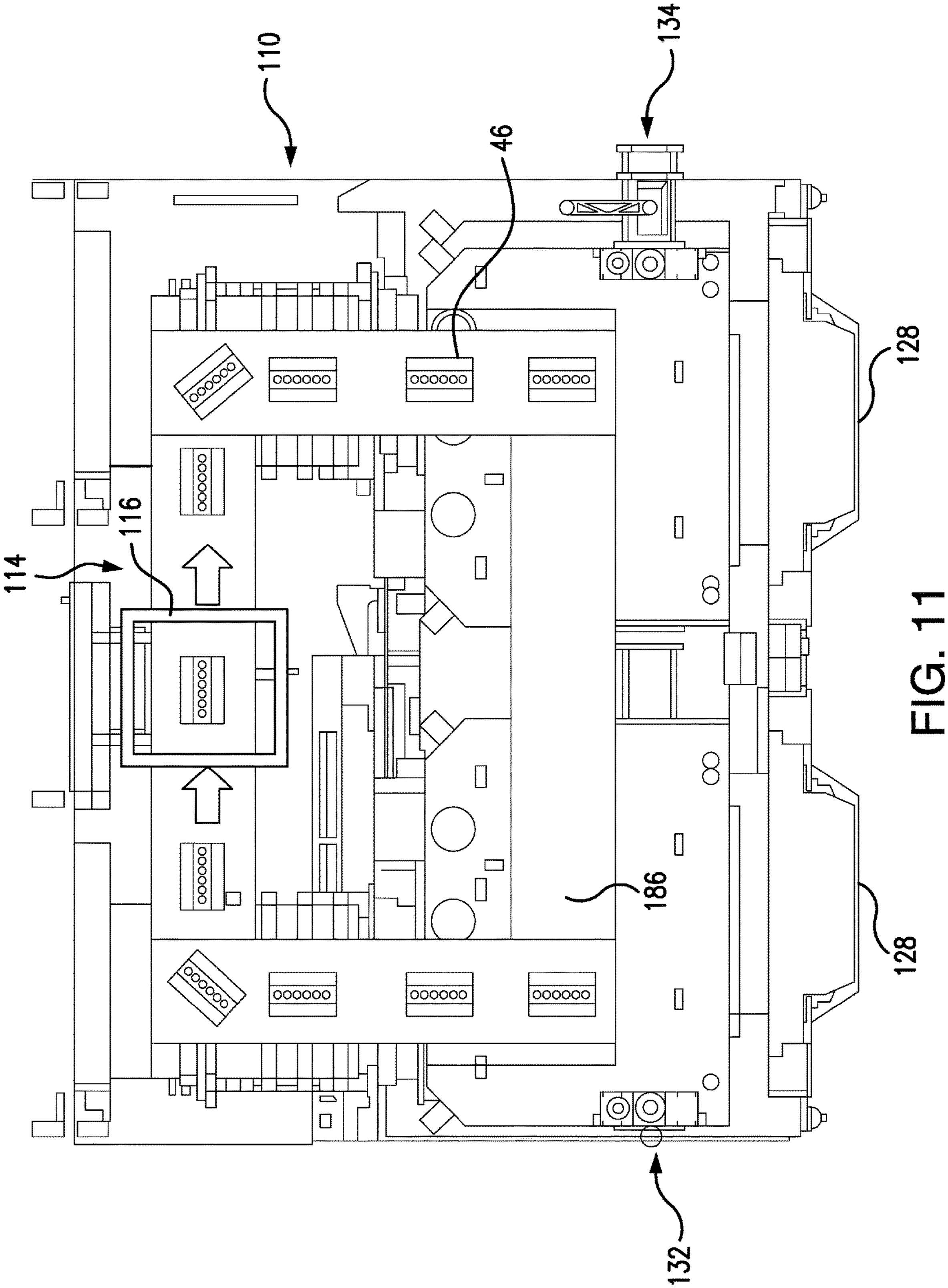
FIG. 11 is a top view of an alternate embodiment of a hot cell including a sterilization zone in accordance with an alternate embodiment of the present invention.

FIG. 11 illustrates an alternate embodiment of a hot cell 110 including a sterilization system 114 having a recirculating conveyor concept. Specifically, nests 46 including the radiopharmaceutical products are placed on a conveyor 186 by manipulators after entering the hot cell 110 from the entrance port 132. Each nest 46 is moved along the conveyor 186 until it is exposed to E-beam flux in an active area 116 (sterilization zone) beneath an accelerator 24, with the nests 46 that have been sterilized being removed from the hot cell 110 through the exit port 134. Note, two windows 128 may preferably be provided to allow one operator to position the nests 46 on the conveyor 186 with one set of manipulators while another operator removes the nests 46 from the conveyor with a second set of manipulators.

Figure 12:
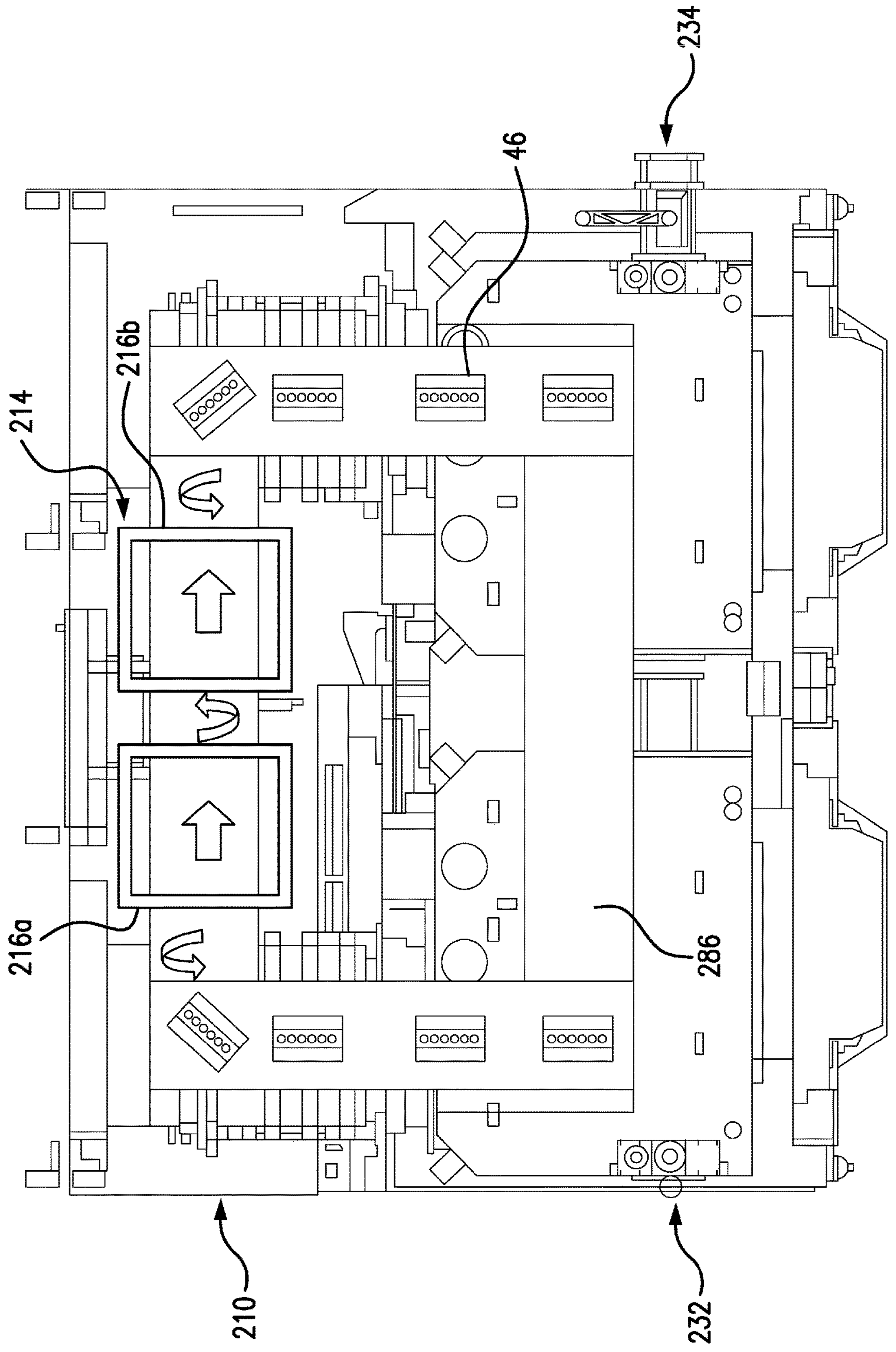
FIG. 12 is a top view of an alternate embodiment of a hot cell including a sterilization zone in accordance with an alternate embodiment of the present invention.

Referring now to FIG. 12, another alternate embodiment of a hot cell 210 having a sterilization system 214 that operates similarly to the embodiment discussed in FIG. 11, with the exception that two active areas 216*a* and 216*b* for exposure to E-beam flux are provided. As shown, each nest 46 moves along the conveyor 286 until being exposed to E-beam flux in a first active area 216*a* after which the nest is rotated 180° and exposed to electron beam flux in a second active area 216*b*. Flipping each nest between E-beam flux exposure allows for the use of a lower power E-beam accelerator 24 assembly than in the embodiment shown in FIG. 11.

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

What is claimed is:

1. A sterilization system for a radiopharmaceutical product, comprising:
- a clean room;
- a hot cell disposed within the clean room;
- a sterilization shaft extending between a first end and a second end and defining an interior, the first end being disposed within the hot cell and the second end being disposed externally to and above the clean room;
- an electron beam accelerator assembly disposed within the interior of the sterilization shaft so that an emission end of the electron beam accelerator assembly is adjacent the first end of the sterilization shaft; and
- a transmission window at the first end of the sterilization shaft so as to separate the interior of the sterilization shaft from the clean room while allowing passage of energy from the emission end of the electronic beam accelerator assembly,
- wherein the electron beam accelerator assembly is vertically removable from the interior of the sterilization shaft to a retracted position.

2. The sterilization system of claim 1, further comprising a sterilization tunnel that is disposed within the hot cell adjacent the first end of the sterilization shaft.

3. The sterilization system of claim 1, wherein the transmission window comprises titanium.

4. The sterilization system of claim 1, wherein:
- the electron beam accelerator assembly is vertically mounted in the sterilization shaft; and
- the sterilization tunnel is located vertically below the sterilization shaft.

5. The sterilization system of claim 2, further comprising a shuttle assembly operative to move the radiopharmaceutical product into and out of the sterilization tunnel.

6. The sterilization system of claim 5, wherein the shuttle assembly is operative to move the radiopharmaceutical product into and out of the sterilization tunnel twice, yielding a first sweep and a second sweep.

7. The sterilization system of claim 6, wherein the shuttle assembly orients the radiopharmaceutical product in a first orientation during the first sweep and a second orientation during the second sweep.

8. The sterilization system of claim 7, wherein the second orientation is rotated by 180° with respect to the first orientation.

9. The sterilization system of claim 8, wherein the shuttle assembly is operative to rotate automatically the radiopharmaceutical product from the first orientation to the second orientation at a time between the first sweep and the second sweep.

10. The sterilization system of claim 5, wherein the shuttle assembly is operative to separate the radiopharmaceutical product from a nest in which the radiopharmaceutical product is carried.

11. The sterilization system of claim 1, wherein at least one guiding rail is provided in the sterilization shaft to facilitate installation and removal of the electron beam accelerator assembly.

12. The sterilization system of claim 1, wherein the sterilization shaft comprises stainless steel-clad tungsten.

13. The sterilization system of claim 11, wherein the at least one guiding rail comprises a pair of guiding rails.

14. The sterilization system of claim 13, wherein the guiding rails are fitted with an end stop for the electron beam accelerator assembly.

15. The sterilization system of claim 14, wherein the sterilization shaft is configured to maintain power and cooling water to the electron beam accelerator assembly when in the retracted position.

* * * * *